US012697110B2

(12) United States Patent
Borut

(10) Patent No.: US 12,697,110 B2
(45) Date of Patent: Aug. 4, 2026

(54) SYSTEMS AND METHODS FOR TISSUE RETRACTION

(71) Applicant: B Side Endeavors LLC, Woodbury, MN (US)

(72) Inventor: Jeffrey J. Borut, Woodbury, MN (US)

(73) Assignee: B Side Endeavors LLC, Woodbury, MN (US)

( * ) Notice: Subject to any disclaimer, the term of this patent is extended or adjusted under 35 U.S.C. 154(b) by 49 days.

(21) Appl. No.: 18/603,612

(22) Filed: Mar. 13, 2024

(65) Prior Publication Data

US 2024/0307049 A1 Sep. 19, 2024

Related U.S. Application Data

(60) Provisional application No. 63/490,699, filed on Mar. 16, 2023.

(51) Int. Cl.
A61B 17/02 (2006.01)
A61B 90/35 (2016.01)
(52) U.S. Cl.
CPC ...... A61B 17/0293 (2013.01); A61B 17/0206 (2013.01); A61B 90/35 (2016.02)

(58) Field of Classification Search
CPC .... A61B 17/0206; A61B 17/0293; A61B 1/32
See application file for complete search history.

(56) References Cited

U.S. PATENT DOCUMENTS

| | | | | |
|---|---|---|---|---|
| 1,919,120 A | * | 7/1933 | Bernard | A61B 17/0293 600/233 |
| 4,010,741 A | * | 3/1977 | Gauthier | A61B 17/0293 600/233 |
| 4,553,537 A | * | 11/1985 | Rosenberg | A61B 17/0293 128/850 |
| 5,460,170 A | | 10/1995 | Hammerslag | |
| 7,390,298 B2 | | 6/2008 | Chu | |
| 7,582,058 B1 | * | 9/2009 | Miles | A61B 17/0293 607/2 |
| 8,961,410 B2 | | 2/2015 | Albrecht et al. | |
| 11,259,791 B2 | * | 3/2022 | Maher | A61B 17/42 |
| 11,278,271 B2 | | 3/2022 | Hart et al. | |
| 2005/0171405 A1 | | 8/2005 | Rowland et al. | |
| 2024/0197308 A1 | * | 6/2024 | Shirazi | A61B 17/0206 |

* cited by examiner

*Primary Examiner* — Larry E Waggle, Jr.
(74) *Attorney, Agent, or Firm* — Fish & Richardson P.C.

(57) ABSTRACT

Some systems, devices and methods detailed herein provide adjustable tissue retraction, for example, to maintain an access opening during a surgical procedure.

16 Claims, 17 Drawing Sheets

100

108

104a

104d

106c

106a

106d

106b

SYSTEMS AND METHODS FOR TISSUE RETRACTION

CROSS-REFERENCE TO RELATED APPLICATION

This application claims priority under 35 U.S.C. § 119 to U.S. Application Ser. No. 63/490,699, filed on Mar. 16, 2023, the contents of which is hereby incorporated by reference.

TECHNICAL FIELD

This document describes systems, devices, and methods for retracting one or more layers of tissue, such as tissue that is proximate to a surgical incision in a patient.

BACKGROUND

Some surgical procedures include creating an incision and retracting tissue layers from the incision to provide an access opening through which a surgeon can perform an operation upon an internal organ or other bodily tissue. In some cases, blades of a retractor device can be inserted into the incision and used to spread various layers of tissue, such as the skin, fascia, muscles, and organs, and then retain those layers of tissue in a retracted position. For example, some conventional modular retractors for abdominal surgeries have a retractor frame that is table-mounted (i.e., the retractor is mechanically mounted to the operating table via an articulating arm or other mechanical external anchor) and that receives a plurality of modular accessories (e.g., paddles, blades, etc.) for mounting to the frame. The sequence of tasks for anchoring this type of conventional modular retractor to a surgical table and then manually attaching its various accessories can be time consuming, especially during an open surgical procedure for a medically urgent situation.

SUMMARY

Some embodiments of the systems, devices, and methods described herein include a retractor configured for rapid deployment in establishing access opening through which a surgeon can perform an operation upon an internal organ or other bodily tissue. In particular implementations, the retractor can include an expandable frame having a set of fixed blades configured for initial retraction of skin and muscle layers in response to adjustment of the expandable frame to an expanded position in which it is lockable, and furthermore having frame mounts configured to releasably receive one or more adjustable paddles for maintaining the access opening in a customized arrangement conveniently selected by a surgeon or other user. In various embodiments, one or more of the fixed blades and adjustable paddles can include light-emitting elements, thereby providing selectable and customizable lighting into the access opening. Further, in some optional embodiments of the systems, devices, and methods described herein, the retractor device can be readily deployed to maintain the access opening throughout the duration of a surgery as a patient-anchored assembly rather than a table-mounted assembly.

Some embodiments described herein include a surgical retractor device. The surgical retractor device includes a four-bar linkage frame that includes four curved arms that are adjustable with respect to each other; at least four fixed blades that extend from the four curved arms; and a lock actuator attached to one or the four curved arms, the lock actuator mechanically controls adjustability the four bar linkage frame, the lock actuator is moveable between a locked position and an unlocked position.

Some embodiments may include one or more of the following optional features. The surgical retractor device where the surgical retractor device is adjustable between a collapsed position and an expanded position by adjusting the four curved arms with respect to each other, and the frame is lockable at a plurality of positions from the collapsed position to the expanded position. The surgical retractor device where, responsive to the lock actuator being moved into the unlocked position, the four bar linkage frame is adjustable between the collapsed position and the expanded position; and responsive to the lock actuator being moved into the locked position, the four bar linkage frame is locked in a position the four curved arms are in when the lock actuator is moved into the locked position. Movement of any of the four curved arms urges movement of the other curved arms. The surgical retractor device may include one or more flexible paddles that are removably attachable to the four bar linkage frame. The one or more flexible paddles are longer than the fixed blades. The one or more flexible paddles include a light source. The four curved arms may include a first set of arms and a second set of arms, the second set of arms being longer than the first set of arms. The fixed blades extend from the second set of arms. The fixed blades may include at least one light source.

Some embodiments described herein include a surgical retractor device. The surgical retractor device includes a frame that includes a plurality of arms that are adjustable with respect to each other; a plurality of fixed blades that extend from the plurality of arms, one or more flexible paddles releasably mounted to the frame between the fixed blades, and a light port that receives a light source connection, where light emitting elements within one or more of the fixed blades and the flexible paddles illuminate in response to light energy delivery from the light port.

Some embodiments may include one or more of the following optional features. The surgical retractor device where the surgical retractor device is adjustable between a collapsed position and an expanded position by adjusting the plurality of arms with respect to each other, and the frame is lockable at a plurality of positions from the collapsed position to the expanded position. The surgical retractor device may include a lock actuator that controls adjustability of the arms, the lock actuator is moveable between a locked position and an unlocked position. The surgical retractor device where, responsive to the lock actuator being moved into the unlocked position, the frame is adjustable between a collapsed position and an expanded position; and responsive to the lock actuator being moved into the locked position, the frame is locked in a position the plurality of arms are in when the lock actuator is moved into the locked position. Movement of any of the plurality of arms urges movement of the other arms. The one or more flexible paddles are longer than the fixed blades.

Particular embodiments herein may include a surgical retractor device. The surgical retractor device includes a frame that includes a plurality of arms that are adjustable with respect to each other; a plurality of fixed blades that extend from the plurality of arms, the plurality of blades having a first length; and one or more flexible paddles releasably mounted to the frame between the fixed blades, the flexible paddles having a second length that is longer than the first length; where the first length is configured for retracting at least one of skin, muscle, and fascia, and the second length is configured for retracting tissues at a greater depth than the first length.

Some embodiments may include one or more of the following optional features. The surgical retractor device where the surgical retractor device is adjustable between a collapsed position and an expanded position by adjusting the plurality of arms with respect to each other, and the frame is lockable at a plurality of positions from the collapsed position to the expanded position. The surgical retractor device may include a lock actuator that controls adjustability of the arms, the lock actuator is moveable between a locked position and an unlocked position. The surgical retractor device where, responsive to the lock actuator being moved into the unlocked position, the frame is adjustable between a collapsed position and an expanded position; and responsive to the lock actuator being moved into the locked position, the frame is locked in a position the plurality of arms are in when the lock actuator is moved into the locked position. Movement of any of the plurality of arms urges movement of the other arms.

In some embodiments, a surgical retractor device includes a frame that includes a plurality of arms that are adjustable with respect to each other; a plurality of fixed blades that extend from the plurality of arms; where surgical retractor device is adjustable between a collapsed position and an expanded position by adjusting the plurality of arms with respect to each other, and the frame is lockable at a plurality of positions from the collapsed position to the expanded position; and where the surgical retractor device is patient-anchored during a surgical procedure.

Some embodiments may include one or more of the following optional features. The surgical retractor device may include a lock actuator that controls adjustability of the arms, the lock actuator is moveable between a locked position and an unlocked position. The surgical retractor device where, responsive to the lock actuator being moved into the unlocked position, the plurality of arms are adjustable between the collapsed position and the expanded position; and responsive to the lock actuator being moved into the locked position, the plurality of arms are locked in a position the plurality of arms are in when the lock actuator is moved into the locked position. The surgical retractor device may include one or more flexible paddles that are removably attachable to the plurality of arms. The one or more flexible paddles are longer than the plurality of fixed blades. The one or more flexible paddles include a light source. The plurality of arms may include a first set of arms and a second set of arms, the second set of arms being longer than the first set of arms. The plurality of fixed blades extend from the second set of arms. The plurality of fixed blades may include at least one light source.

Particular embodiments herein may include a method of retracting tissue. The method of retracting tissue includes inserting a surgical retractor device in a collapsed position into an incision; expanding the surgical retractor device from the collapsed position into an expanded position; and locking the surgical retractor device in the expanded position, where the surgical retractor device is patient-anchored during a surgical procedure.

Some embodiments may include one or more of the following optional features. The method where the surgical retractor device is in an unlocked position when the surgical retractor device is expanded from the collapsed position into the expanded position. The method may include illuminating the surgical retractor device by activating one or more light sources of the surgical retractor device. The surgical retractor device may include a frame that includes a plurality of arms that are adjustable with respect to each other, and a plurality of fixed blades that extend from the plurality of arms. The plurality of fixed blades are inserted into the incision while the plurality of arms remain outside of the incision. The method may include: attaching one or more flexible paddles to the frame; and bending at least one of the one or more flexible paddles into the incision such that the at least one flexible paddle extends into the incision further than the plurality of fixed blades. The method may include adjusting a position of at least one of the one or more flexible paddles along the frame.

In an example embodiment, a retractor system includes a frame that includes a plurality of curved arms that are adjustable with respect to each other, and a plurality of fixed blades that extend from the plurality of curved arms; a lock actuator that controls adjustability of the curved arms, the lock actuator is moveable between a locked position and an unlocked position; where, responsive to the lock actuator being moved into the unlocked position, the plurality of curved arms are adjustable between a collapsed position and an expanded position; and responsive to the lock actuator being moved into the locked position, the plurality of arms are locked in a position the plurality of arms are in when the lock actuator is moved into the locked position.

Some embodiments may include one or more of the following optional features. The retractor system where the plurality of arms may include a first set of arms and a second set of arms, the second set of arms being longer than the first set of arms. The retractor system may include one or more flexible paddles that are removably attachable to the frame. The frame may include at least one light source.

In an example embodiment, a flexible retractor paddle includes a bracket that is configured to removably attach the flexible retractor paddle to a frame of a surgical retractor system; a paddle portion that is pliable and configured to be bent into a plurality of positions.

Some embodiments may include one or more of the following optional features. The flexible retractor paddle may include a light source at the paddle portion. The bracket is configured to connect to a terminal on the frame of the retractor system. The flexible retractor paddle may include a power source that is connected to one or more light sources of the flexible retractor paddle. The flexible retractor paddle may include one or more openings configured for removal of vapor from an access opening.

In an example embodiment, a retractor system includes a frame that includes a plurality of curved arms that are adjustable with respect to each other, and a plurality of fixed blades that extend from the plurality of curved arms; a lock actuator that controls adjustability of the curved arms, the lock actuator is moveable between a locked position and an unlocked position; and a surgical drape that has a drape frame, the drape frame includes one or more pliable members that are formable into various shapes and positions; where, responsive to the lock actuator being moved into the unlocked position, the plurality of curved arms are adjustable between a collapsed position and an expanded position; and responsive to the lock actuator being moved into the locked position, the plurality of arms are locked in a position the plurality of arms are in when the lock actuator is moved into the locked position.

In an example embodiment, a retractor system includes a frame that includes a plurality of curved arms that are adjustable with respect to each other, and a plurality of fixed blades that extend from the plurality of curved arms; a lock actuator that controls adjustability of the curved arms, the lock actuator is moveable between a locked position and an unlocked position; and where, responsive to the lock actuator being moved into the unlocked position, the plurality of curved arms are adjustable between a collapsed position and an expanded position; and responsive to the lock actuator being moved into the locked position, the plurality of arms are locked in a position the plurality of arms are in when the lock actuator is moved into the locked position; where at least one of the frame and the fixed blades includes one or more openings, the one or more openings are connected to a suction source that is configured to apply a suction to the one or more openings to remove vapor from an access opening maintained by the retractor system.

Some embodiments may include one or more of the following optional features. The retractor system may include a flexible paddle that is removably mountable to the frame, the flexible paddle has one or more openings that are connected to the suction source that is configured to apply a suction to the one or more openings to remove vapor from an access opening maintained by the retractor system.

In an example embodiment, a retractor system includes a frame that includes a plurality of curved arms that are adjustable with respect to each other, a plurality of fixed blades that extend from the plurality of curved arms; a lock actuator that controls adjustability of the curved arms, the lock actuator is moveable between a locked position and an unlocked position; an imaging device that is removably mountable to the frame, and where, responsive to the lock actuator being moved into the unlocked position, the plurality of curved arms are adjustable between a collapsed position and an expanded position; and responsive to the lock actuator being moved into the locked position, the plurality of arms are locked in a position the plurality of arms are in when the lock actuator is moved into the locked position.

Particular embodiments described herein can provide one or more of the following advantages. First, some embodiments of the systems, devices, and methods described herein provide a more efficient approach to retracting various tissue layers to provide an access opening.

Second, a number of embodiments described herein offer a solution for a retractor device that can be releasably lockable at customized positions from a collapsed position to an expanded position to retract various tissue layers to establish an access opening.

Third, some embodiments described herein can provide a rapidly deployable retractor device that maintains the access opening throughout the duration of a surgery without requiring mechanical external anchoring to an operating table, which can reduce the amount of tasks in mounting the retractor device and can reduce the amount of mechanical obstructions in surgical area extending from the retractor device. For example, some optional embodiments include a patient-anchored retractor device rather than a table-mounted retractor. (As used herein, the term "patient-anchored" means that the assembly is safely mountable to a patient throughout the duration of a surgery without being mechanically anchored to the operating table via an articulating arm or other mechanical external anchor.)

Fourth, some implementations of the systems, devices, and methods described herein provide an improved user experience by facilitating a streamlined process for retracting the various tissues to create the access opening. The systems, devices, and methods described herein provide modular features can also be implemented in some example embodiments that improve the user's experience by retracting additional tissues and organs within the surgical working area and illuminating the surgical area without the intervention of separately inserted lighting instrument that might otherwise obstruct or occupy portions of the access opening.

Fifth, some embodiments described in more detail below can achieve a disposable, one-time-use retractor device that provides cost-effective disposal of particular components that contact a patient during surgery and detachability of more complex components (e.g., for optional reuse of the detachable components).

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
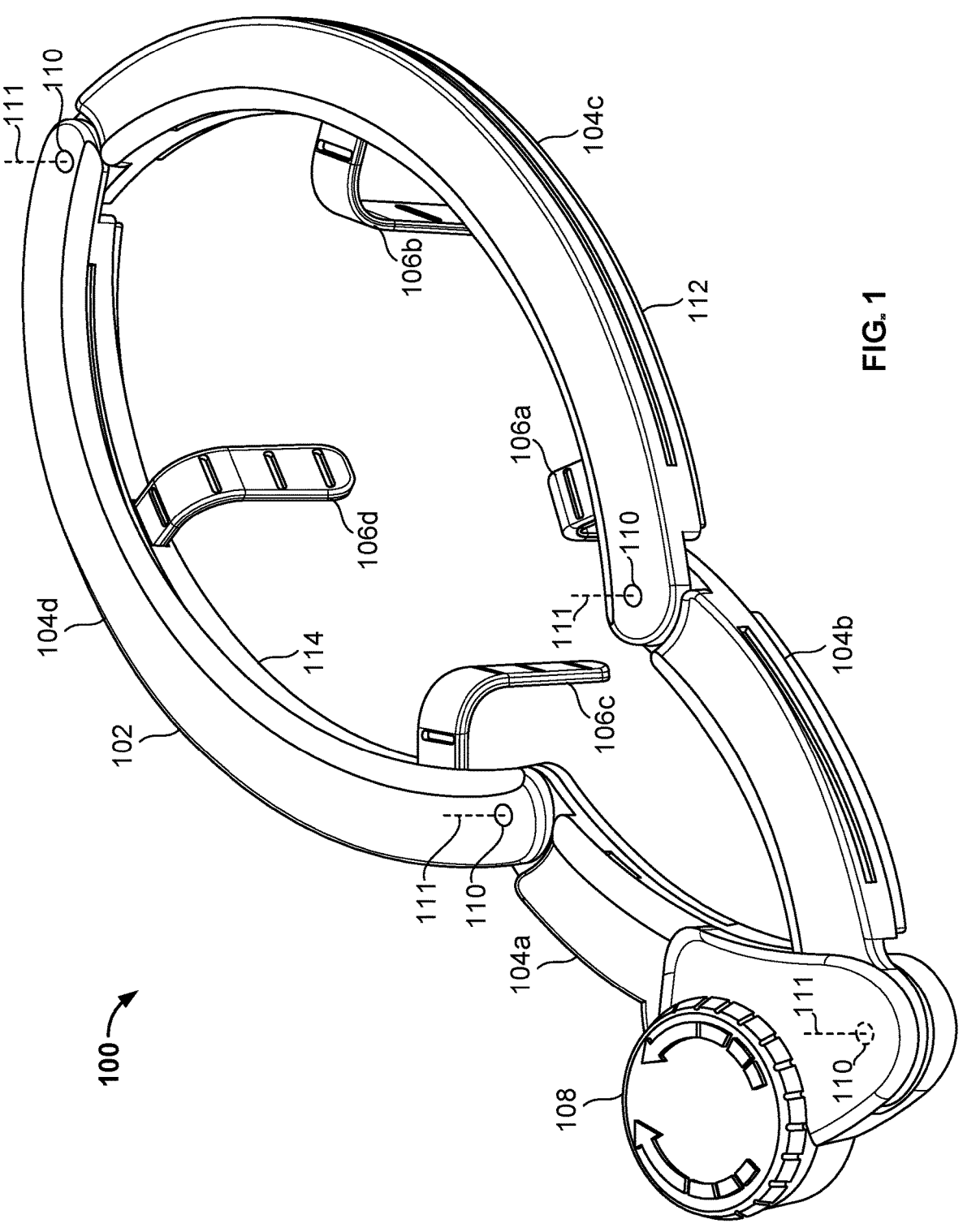
FIG. 1 shows a perspective view of an example surgical retractor device in a collapsed position, consistent with some embodiments of this disclosure.
Figure 2:
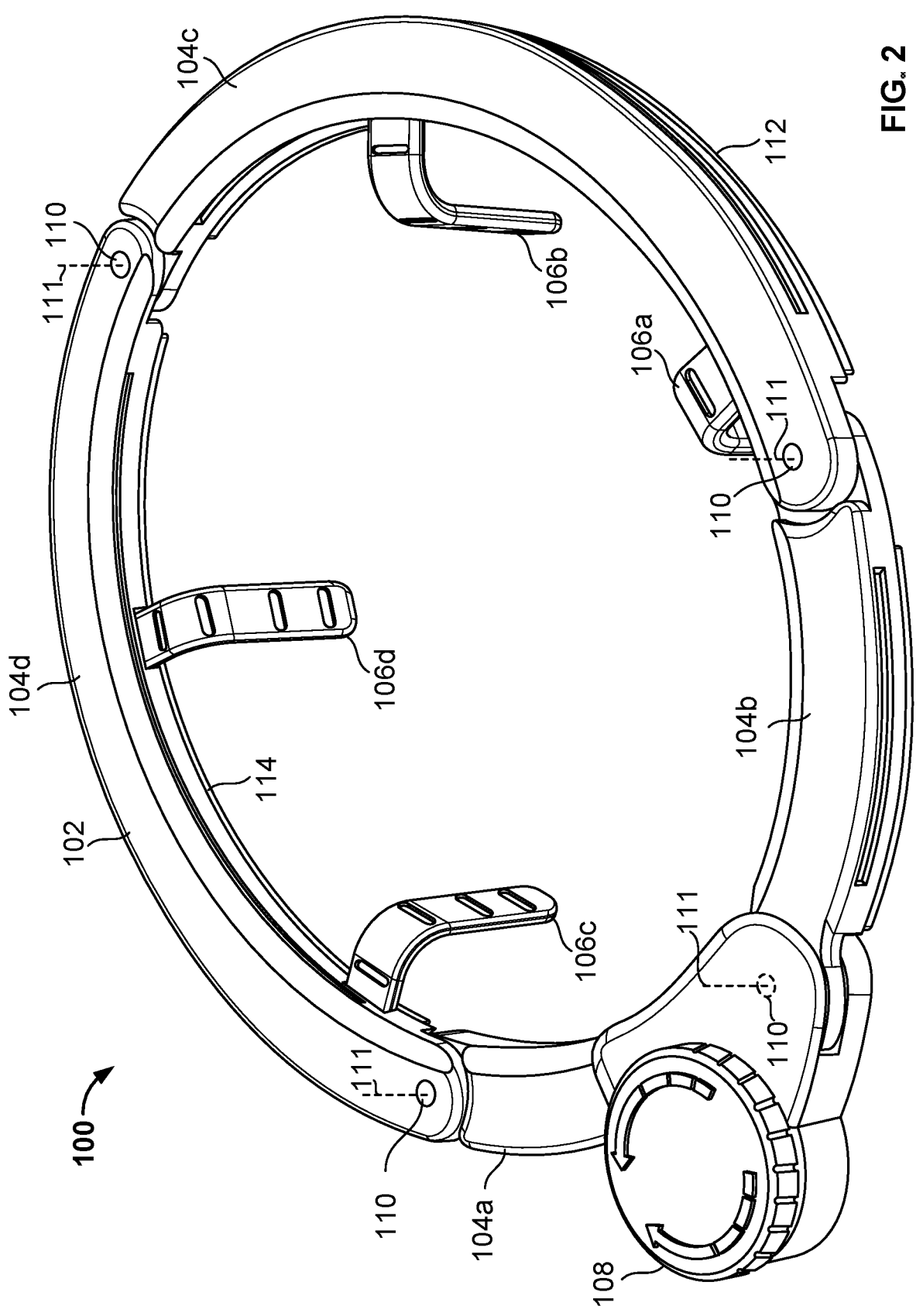
FIG. 2 shows a perspective view of the surgical retractor device of FIG. 1 in an expanded position.

Referring to FIGS. 1 and 2, some embodiments of a surgical retractor device 100 are configured to retract various tissue layers of a subject to provide an access opening for medical personnel. In the depicted embodiment, the surgical retractor device 100 is an adjustable surgical retractor device 100 that is adjustable between a collapsed position (e.g., FIG. 1) and an expanded position (e.g., FIG. 2). As detailed below, the surgical retractor device 100 can releasably lock into one or more positions between the collapsed position and the expanded position to safely retract various tissue layers to maintain an access opening that provides a surgeon or other medical personnel consistent access to areas of treatment in the subject.

The surgical retractor device 100 can include a frame 102 that has a plurality of arms 104a, 104b, 104c, 104d, a plurality of fixed blades 106a, 106b, 106c, 106d, and a lock actuator 108. The plurality of arms 104a, 104b, 104c, 104d of the frame 102 are adjustable with respect to each other. For example, the surgical retractor device 100 can include four arms 104a, 104b, 104c, and 104d that are connected via one or more hinges 110 to form the frame 102. In the depicted embodiment, the arm 104a is connected to the arm 104b via a hinge 110 and is connected to the arm 104d via a hinge 110. The arm 104b is also connected to the arm 104c via a hinge 110, and the arm 104c is connected to the arm 104d via a hinge 110. The hinges 110 between each arm 104a, 104b, 104c, 104d facilitate movement of the arms 104a, 104b, 104c, 104d with respect to each other where the arms 104a, 104b, 104c, 104d rotate about the hinges 110 to expand and collapse the frame 102.

In some embodiments, the frame 102 is formed as a linkage, such as a four-bar linkage frame that includes the four arcuate arms 104a, 104b, 104c, and 104d. Movement of two arms relative to one another urges movement of all the arms 104a, 104b, 104c, and 104d of the linkage frame. For example, a user (e.g., a surgeon or other user) can move the arm 104c from the collapsed position shown in FIG. 1 to the expanded position in FIG. 2. The arm 104c moves relative to the arms 104b and 104d that the arm 104c is connected to via hinges 110, and the movement of the arm 104c urges the movement of the arms 104b and 104d that are connected to the arm 104c. The movement of the arms 104b, 104c, and 104d also urges the movement of the arm 104a of the linkage frame. As described in more detail below (e.g. FIGS. 11A-C), a user can impart movement on any of the arms 104a, 104b, 104c, and 104d to urge the movement of the other arms 104a, 104b, 104c, and 104d.

In some embodiments, the hinges 110 each include a hinge axis 111 that that define a relative pivoting movement of the adjoining arm 104a, 104b, 104c, or 104d. In the depicted embodiment, all of the hinge axes 111 are parallel to each other, and the arms 104a, 104b, 104c, and 104d extend in a shared plane that is perpendicular to the hinge axes 111 of each hinge 110. Each of the arms 104a, 104b, 104c, and 104d in the depicted embodiment include an arcuate shape extending in the shared plane such that the arms 104a, 104b, 104c, and 104d can collectively provide an ovular shape (e.g., a circle, an ellipse, or an oval) in the shared plane (refer, for example, to FIG. 2).

In the depicted embodiment, the arms 104a and 104b each have a length that is less than a length of each of the arms 104c, 104d. For example, arms 104a and 104b can have a first length and arms 104c, and 104d can have a second length, where the first length is shorter than the second length. In some embodiments, arms 104a and 104b can have different lengths and arms 104c and 104d can have equal or nearly equal lengths (e.g., within a 5% difference). In some embodiments, the plurality of arms 104a, 104b, 104c, 104d can include a first set of arms (e.g., arms 104a, 104b) and a second set of arms (e.g., arms 104c, 104d). The first set of arms (e.g., the arms 104a and 104b) can have lengths that are less than the lengths of the second set of arms (e.g., arms 104c, 104d).

The plurality of arms 104a, 104b, 104c, and 104d can each have a curved profile in the common plane that includes a convex outer profile 112 and a concave inner profile 114. The convex outer profile 112 of each arm 104a, 104b, 104c, 104d can include a similar or equal angle of curvature such that in the expanded position (see e.g., FIG. 2), the outer profile 112 of the respective arms 104a, 104b, 104c, and 104d align with each other to form a continuous or nearly continuous outer profile 112. The concave inner profile 114 of each arm 104a, 104b, 104c, 104d can include a similar or equal angle of curvature such that in the expanded position (see e.g., FIG. 2), the inner profile 114 of the respective arms 104a, 104b, 104c, and 104d align with each other to form a continuous or nearly continuous inner profile 114.

Still referring to the depicted embodiment in FIGS. 1 and 2, the lock actuator 108 controls locked/unlocked condition of the frame 102 of surgical retractor device 100. For example, the lock actuator 108 comprises an adjustable actuator that can be shifted from an unlocked position to a locked position so as to lock the position of the arms 104a and 104b relative to one another. The actuator 108 can, for example, urge an interior clamp mechanism to retain the second arm 104b in a user-selected position about the hinge 110 relative to the first arm 104a. Because the arms 104a-d of the frame 102 are arranged as a mechanical linkage (e.g., a four bar linkage frame) in the depicted embodiment, using the lock actuator 108 to rigidly retain the second arm 104b in a fixed position relative to the first 104a will also result in all of the arms 104a-d being rigidly retained in the user-selected position. As such, the lock actuator 108 can control the adjustability of the plurality of arms 104a, 104b, 104c, 104d of the frame 102. In the depicted embodiment, the surgical retractor device 100 includes a single lock actuator 108 that locks and unlocks the arms 104a, 104b, 104c, 104d from movement relative to each other. In some embodiments, the surgical retractor device 100 includes two or more lock actuators 108 positioned around the frame 102 to lock and unlock the arms 104a, 104b, 104c, 104d from movement relative to each other, thereby providing added safety and redundancy for locking the frame 102 in an orientation selected by the user.

The lock actuator 108 is moveable between a locked position and an unlocked position. Responsive to the lock actuator 108 being moved into the unlocked position, the plurality of arms 104a, 104b, 104c, 104d are adjustable between the collapsed position (e.g., FIG. 1) and the expanded position (e.g., FIG. 2). Responsive to the lock actuator 108 being moved into the locked position, the plurality of arms 104a, 104b, 104c, 104d are locked in a position the plurality of arms 104a, 104b, 104c, 104d are in when the lock actuator 108 is moved into the locked position. In some embodiments, the lock actuator 108 can be a ratcheting mechanism that can be rotated in a first direction to tighten the lock actuator 108 into the locked position, and the ratcheting mechanism can be released or unlocked (e.g., by engaging a pin, a release button, toggling a lever, etc.) to rotate in a second direction to loosen the lock actuator 108 into the unlocked position.

Figure 3:
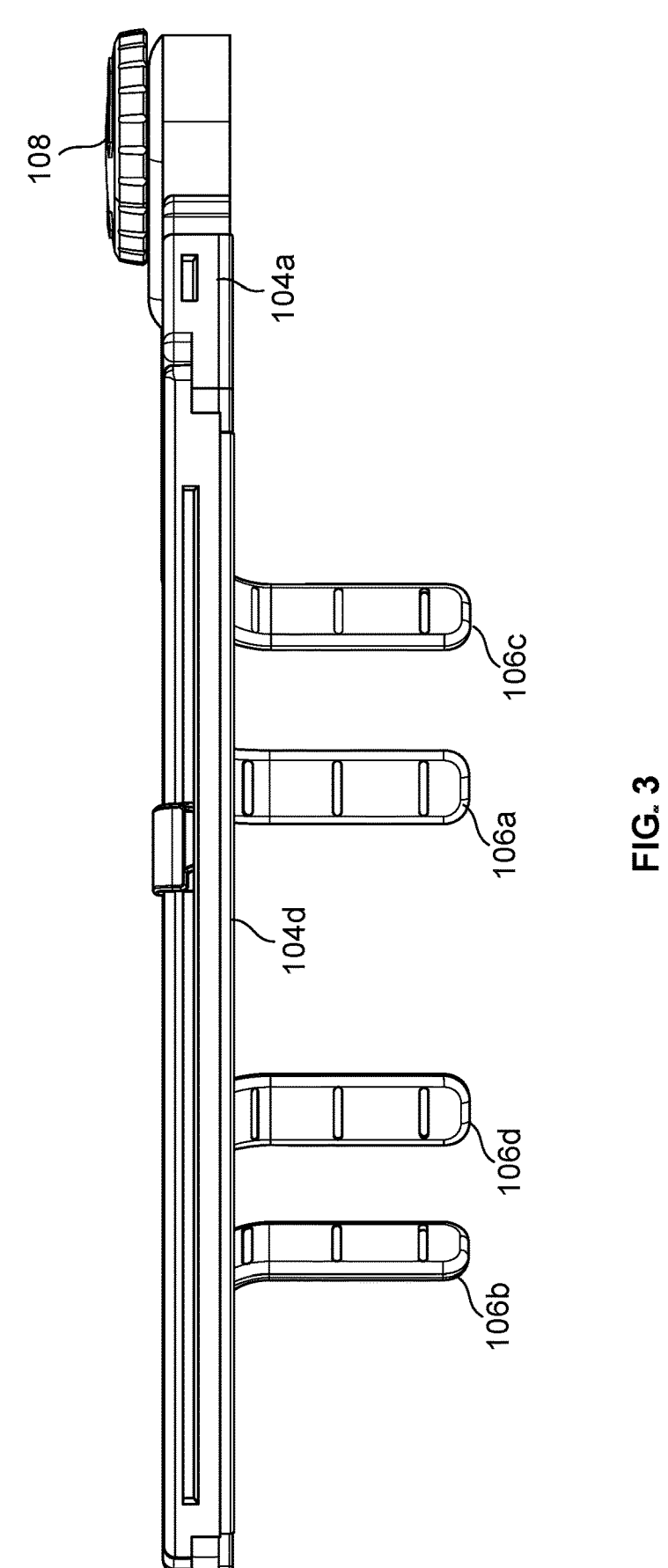
FIG. 3 shows a side view of the surgical retractor device of FIG. 2.

Referring to FIGS. 1-3, the surgical retractor device 100 includes the plurality of fixed blades 106*a*, 106*b*, 106*c*, 106*d* that extend from the plurality of arms 104*a*, 104*b*, 104*c*, 104*d*. In some embodiments, the plurality of fixed blades 106*a*, 106*b*, 106*c*, 106*d* are connected to and extend from the arms 104*c*, 104*d* along the inner profile 114 of the arms 104*c*, 104*d*. The fixed blades 106*a*, 106*b*, 106*c*, 106*d* can extend from the inner profile 114 and bend downward. In some aspects, the fixed blades 106*a*, 106*b*, 106*c*, 106*d* extend in a direction that is perpendicular to the arms 104*a*, 104*b*, 104*c*, 104*d* that extend in the common plane. In some embodiments, each of the fixed blades 106*a*, 106*b*, 106*c*, 106*d* can have equal lengths. In other embodiments, the fixed blades 106*a*, 106*b*, 106*c*, 106*d* can optionally have variable lengths.

In the depicted embodiment, the fixed blades 106*a*, 106*b*, 106*c*, 106*d* are rigid or semi-rigid such that the fixed blades 106*a*, 106*b*, 106*c*, 106*d* contact the various tissue layers of a subject and retract the various tissue layers responsive to the surgical retractor device 100 being expanded from the collapsed position (e.g., FIG. 1) to the expanded position (e.g., FIG. 2). The blades 106*a*, 106*b*, 106*c*, and 106*d* are rigidly and fixedly mounted to the frame 102 so as to move together with the arms 104*a*, 104*b*, 104*c*, and 104*d* of the frame 102. As described in more detail below (e.g. FIGS. 11A-C), the fixed blades 106*a*, 106*b*, 106*c*, and 106*d* can provide a useful solution during the initial retraction of bodily tissue to provide an interior space for insertion of additional releasably mountable accessories.

Figure 4:
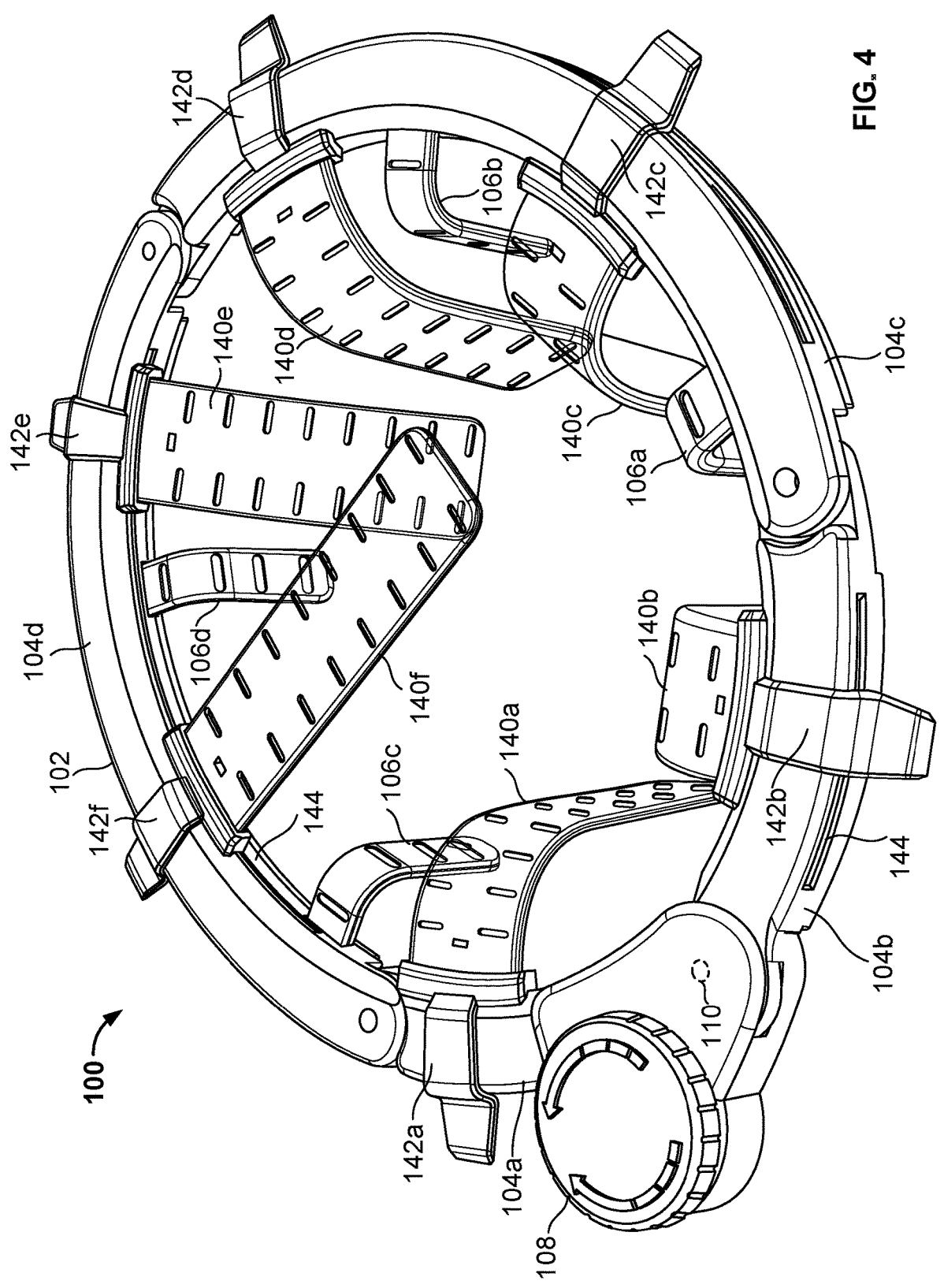
FIG. 4 shows a perspective view of the surgical retractor device of FIG. 2 with a plurality of modular accessories, consistent with some embodiments of this disclosure.
Figure 5:
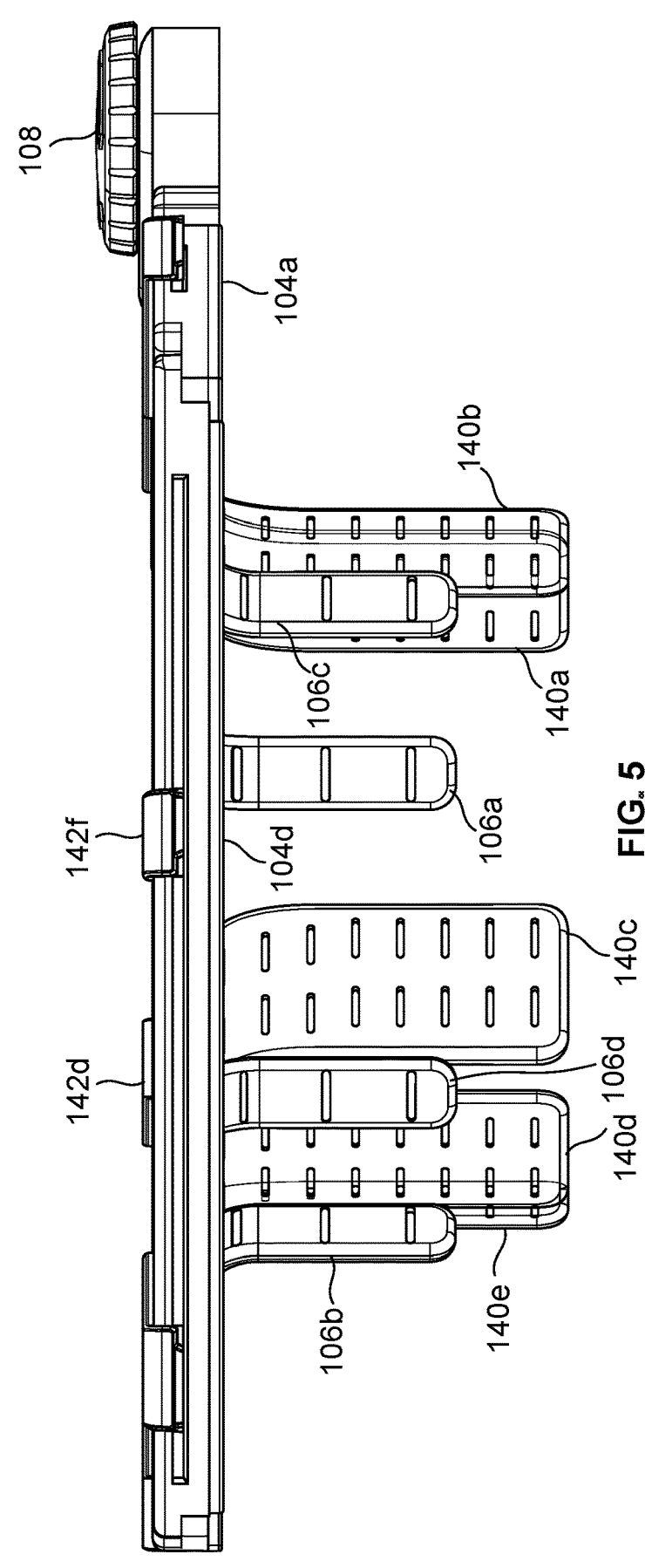
FIG. 5 shows a side view of the surgical retractor device of FIG. 4.

Referring to FIGS. 4 and 5, the surgical retractor device 100 is shown with a plurality of modular accessories that are releasably mounted to the frame 102. In some embodiments, the modular accessories can include a plurality of flexible paddles 140*a*-140*f* that are releasably mounted to the frame 102 after the frame 102 is adjusted from a collapsed position to an expanded position. The plurality of flexible paddles 140*a*-140*f* are each flexible and configured to be manually bent during a surgery into user-selected orientations relative to the frame 102. In some embodiments, the plurality of flexible paddles 140*a*-140*f* are pliable and configured to be bent into a custom orientation, yet are sufficiently resilient after being bent so as to remain in the custom orientation to maintain bodily tissue in a retracted condition (e.g., until a user bends the flexible paddles 140*a*-140*f* out of the custom orientation into another orientation). The flexible paddles 140*a*-140*f* are flexible to be bent and maneuvered into custom orientations, while maintaining rigidity to retract tissues and organs when the flexible paddles 140*a*-140*f* are positioned in the custom orientation.

Each of the plurality of flexible paddles 140*a*-140*f* can include a mount bracket 142*a*-142*f* that facilitates releasable mating with, and removal from, the frame 102. The brackets 142*a*-142*f* can extend over a respective arms 104*a*-*d* of the frame 102 and engage with or clip to the frame 102 to hold the plurality of flexible paddles 140*a*-142*f* to the frame 102. In some embodiments, the brackets 142*a*-142*f* connect to the frame 102 and engage with a mating groove 144 defined in an outer face of each arm 104*a*-104*d*. Optionally, each arm 140*a*-104*d* can include a groove 144 on both outer face (e.g., oriented to face away from the surgical opening) and the inner face (e.g., oriented to face toward the surgical opening) of the respective arm 104*a*-104*d* that receives a portion of the brackets 142*a*-142*f* to engage with and connect the plurality of flexible paddles 140*a*-140*f* to the frame 102. The plurality of brackets 142*a*-142*f* can releasably connect to the frame 102 via an interference fit, a friction fit, a snap fit, or a threaded connection. The plurality of flexible paddles 140*a*-140*f* can be connected to any of the arms 104*a*-104*d* of the frame 102. The plurality of flexible paddles 140*a*-140*f* can be moveable, slidable, or otherwise adjustable along the arms 104*a*-104*d* to provide a customizable and adjustable orientation of the plurality of flexible paddles 140*a*-140*f*.

The surgical retractor device 100 can include multiple different modular accessories configured to releasably mate with the frame 102, including the flexible paddles 140*a*-140*f*. For example, the depicted embodiment in FIG. 4 includes six flexible paddles 140*a*-140*f*, with the flexible paddle 140*a* connected to the arm 104*a*, the flexible paddle 140*b* connected to the arm 104*b*, the flexible paddles 142*c*, 142*d* connected to the arm 104*c*, and the flexible paddles 140*e*, 140*f* connected to the arm 104*d*. In other examples, the retractor device 100 can include any number of flexible paddles 140*a*-140*f* including more than six flexible paddles, and the retractor device 100 can include no flexible paddles as depicted in FIG. 2.

The flexible paddles 140*a*-140*f* can be customizable by including any number of flexible paddles, arranging the flexible paddles 140*a*-140*f* into various positions around the frame 102, and bending each of the flexible paddles 140*a*-140*f* into a custom position. The flexible paddles 140*a*-140*f* are adjustable and facilitate rapid movement and adjustment of the position of each of the flexible paddles 140*a*-140*f* around the frame 102 and the custom position of each of the flexible paddles 140*a*-140*f*. For example, flexible paddle 140*a* in in the illustrated embodiment is straight (i.e., unbent) while flexible paddles 140*b*-140*f* are bent to align with the fixed blades 106*a*-106*d*.

In some embodiments, the flexible paddles 140*b*-140*f* can be longer and wider than the fixed blades 106*a*-106*d*. For example, in a bent orientation shown in FIG. 5 where the flexible paddles 140*b*-140*f* are bent to align with the fixed blades 106*a*-106*c*, the flexible paddles 140*b*-140*f* extend further from the frame 102 than the fixed blades 106*a*-106*d*. The shorter length of the fixed blades 106*a*-106*d* can be configured for retracting at least one of skin, muscle, and fascia, and the longer length of the flexible paddles 140*a*-140*f* is configured for retracting tissues at a greater depth than length of the fixed blades 106*a*-106*d*. For example, the fixed blades 106*a*-106*f* can contact and retract at least one of skin, muscle, and fascia that are at or near the surface of the patient's skin to retract the surgical opening and create the access opening (see e.g., access opening 1111 in FIGS. 11B and 11C). The flexible paddles 140*a*-140*f* can extend further or deeper into the access opening to contact, retract, and reposition other tissues such as additional muscle, organs, and other tissues positioned deeper than the tissues retracted by the fixed blades 106*a*-106*d*.

The flexible paddles 140*a*-140*f* improve the user's experience by retracting additional tissues and organs within the surgical working area. For example, the flexible paddles 140*a*-140*f* can contact and retract additional organs, muscles, and other tissue layers that the fixed blades 106*a*-106*b* do not reach, contact, or retract.

Figure 6:
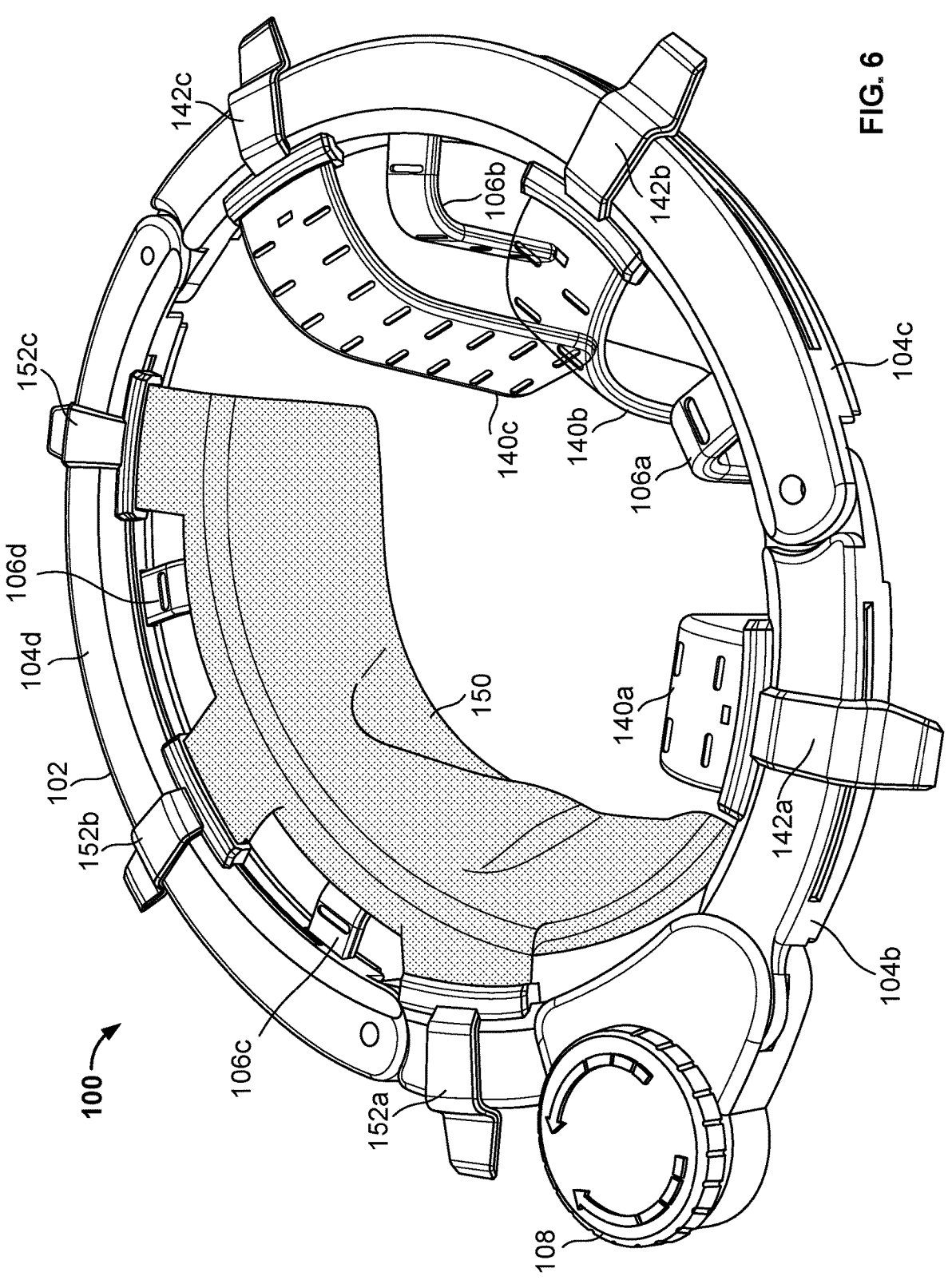
FIG. 6 shows a perspective view of the example surgical retractor device of FIG. 2 with flexible paddles and a retractor drape, consistent with some embodiments of this disclosure.

FIG. 6 shows the surgical retractor 100 with multiple different types of modular accessories that are releasably attached to the frame 102, such as flexible paddles 140*a*-140*c* and a surgical drape 150 that is configured for insertion into the surgical opening for engagement with retracted bodily tissue. The surgical drape 150 can attach to the frame 102 via one or more brackets 152*a*-152*c*. The brackets 152*a*-152*c* can share the features of the brackets 142*a*-142*c* that attach the plurality of flexible paddles 140*a*-140*c* to the frame 102.

In some aspects, the surgical drape 150 includes three brackets 152*a*-152*c* that facilitate connection and removal of the surgical drape 150 to and from the frame 102. While three brackets 152*a*-152*c* are depicted, other embodiments could include one bracket (e.g., bracket 152*b*), two brackets (e.g., brackets 152*a* and 152*c*), or more than three brackets.

In some embodiments, the surgical drape 150 can extend over one or more of the fixed blades (e.g., fixed blades 106*c*, 106*c*) to provide at least one of a covering, padding, shielding, or otherwise partitioning a portion of the surgical retractor device 100. For example, the surgical drape 150 can cover a portion of an access opening that medical personnel to prevent exposure of that portion of the access opening to treatment or operations performed in other areas of the access opening.

Figure 7:
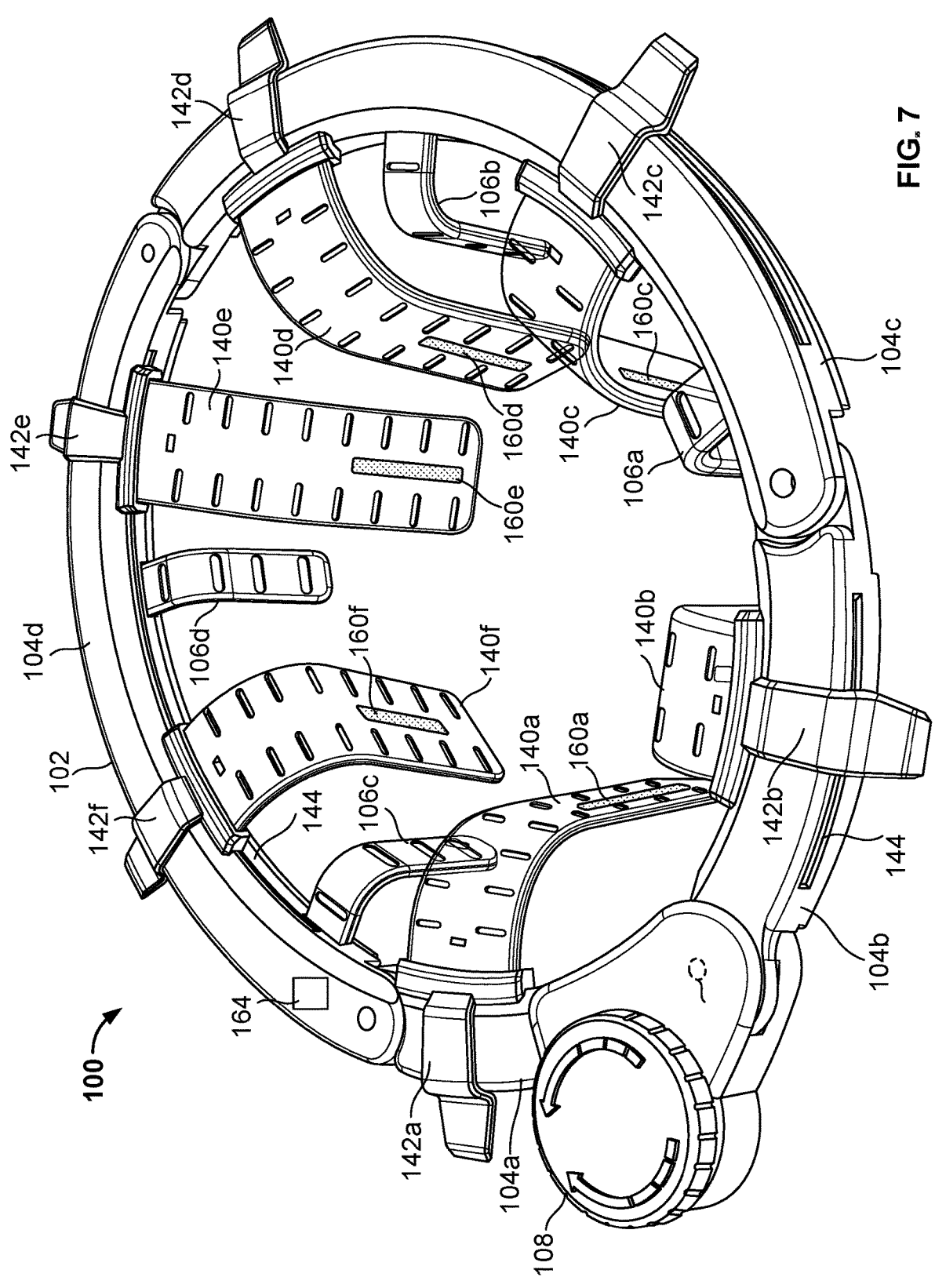
FIG. 7 shows a perspective view of the example surgical retractor device of FIG. 2 with flexible paddles and one or more light sources, consistent with some embodiments of this disclosure.

FIG. 7 shows the surgical retractor 100 in another example having modular accessories that are releasably attached to the frame 102, such as flexible paddles 140*a*-140*f* that include light sources 160*a*-160*f*. In some embodiments, the light sources 160*a*-160*f* can include light-emitting diodes (LEDs), optical fibers, fluorescent light sources, or other light sources that facilitate the illumination of the surgical area. The light sources 160*a*-160*f* can extend along the flexible paddles 140*a*-140*f*, and can be activated to illuminate a surgical area. In some embodiments, the surgical retractor 100 includes a power source 164 that powers the light sources 160*a*-160*f*. In some embodiments, the connection of each flexible paddle 140*a*-140*f* to the frame 102 provides an electric connection between each of the light sources 160*a*-160*f* and the power source 164. For example, each of the brackets 142*a*-142*f* can include an electrical connector that is configured to connect to a connection terminal of the frame 102. In some embodiments, the frame 102 includes a plurality of connection terminals spaced apart around the frame 102 to facilitate custom positioning of the flexible paddles 140*a*-140*f* and connection to the power source 164. The electrical connection between the brackets 142*a*-142*f* and the connection terminal on the frame 102 connects each flexible paddle 140*a*-140*f* to the power source 164. The electrical connection between the brackets 142*a*-142*f* and the connection terminal on the frame 102 powers the light sources 160*a*-160*f*.

In some embodiments, the connection between the frame 102 and each of the brackets 142*a*-142*f* is a fiber optic connection that connects the light sources 160*a*-160*f* to a fiber optic source. For example, the frame 102 can include an optical port (see e.g., optical port 925 in FIG. 9) that can connect to a light source (e.g., light source 927) that provides fiber optic lighting to the surgical retractor device 100. Each of the flexible paddles 140*a*-140*f* can include fiber optic cables that extend from the light sources 160*a*-160*f* and connect to fiber optic cables in the frame 102 that extend to connection at the optical port.

In some embodiments, each flexible paddle 140*a*-140*f* could include a power source (e.g., power source 164) that powers the light sources on each respective flexible arm 140*a*-140*f*. The power source at each flexible paddle 140*a*-140*f* can be positioned at the bracket 142*a*-142*f*, on the flexible paddle 140*a*-140*f*, or within the one or more light sources 160*a*-160*f* to provide power to the light sources 160*a*-160*f*.

The light sources 160*a*-160*f* facilitate customizable lighting for the surgical retractor 100 with modular accessories (e.g., flexible paddles 140*a*-140*f*) and fixed blades 106*a*-

106*d*. The light sources 160*a*-160*f* can illuminate the surgical area without the intervention of separately inserted lighting instruments that might otherwise obstruct or occupy portions of the access opening.

Figure 8:
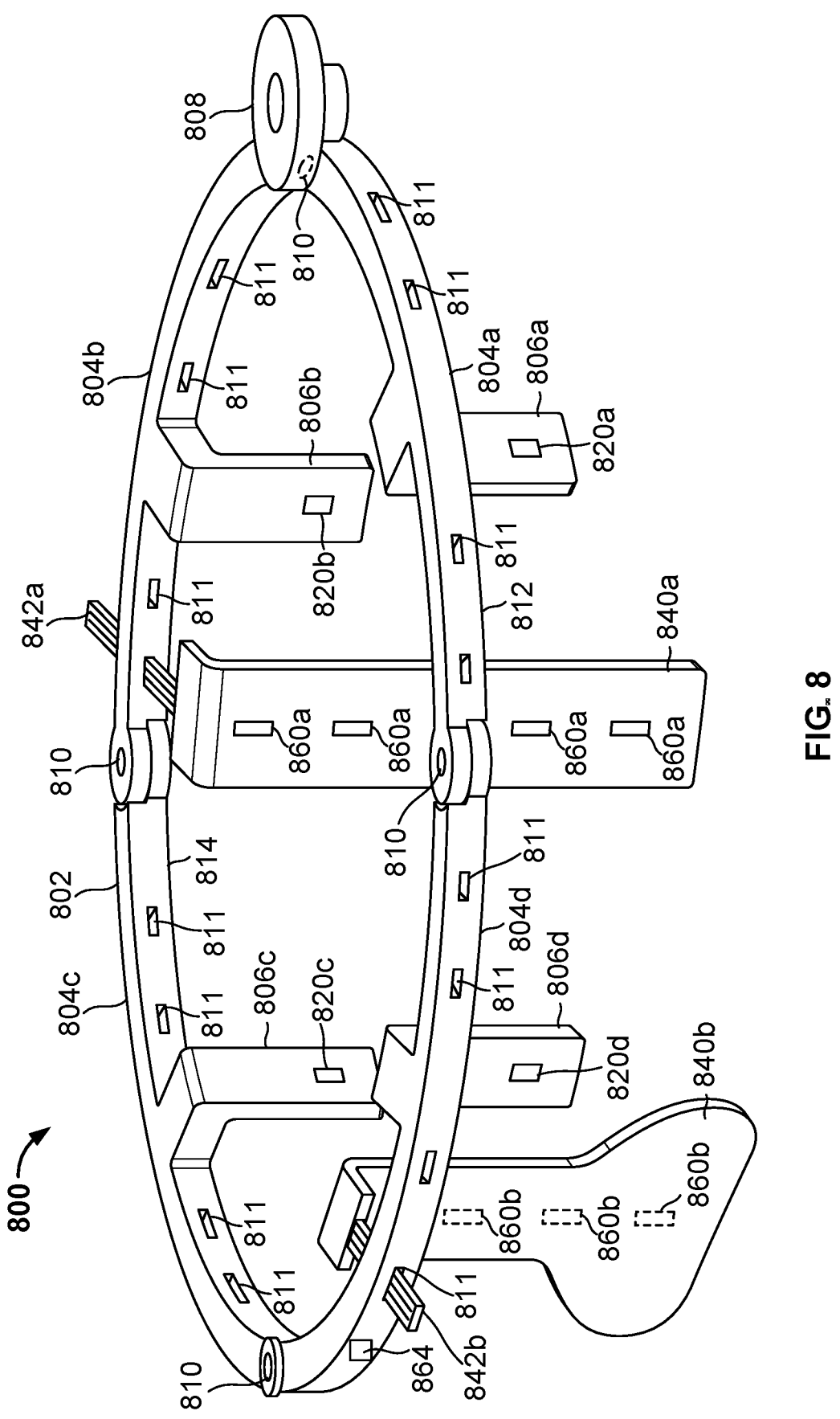
FIG. 8 shows a perspective view of another example surgical retractor device with flexible paddles and one or more light sources, consistent with further embodiments of this disclosure.

Referring to FIG. 8, some embodiments of a surgical retractor device 800 are configured to retract various tissue layers of a subject to provide an access opening for medical personnel. In the depicted embodiment, the surgical retractor device 800 is an adjustable surgical retractor device 800 that is adjustable between a collapsed position and an expanded position (e.g., FIG. 8), as similarly described above in connection with FIGS. 1-2.

The surgical retractor device 800 can share features with the surgical retractor device 100 described above in FIGS. 1-2. For example, the surgical retractor device 800 includes a frame 802 that has a plurality of arms 804*a*-804*d*, a plurality of fixed blades 806*a*, 806*b*, 806*c*, 806*d*, and a lock actuator 808. The frame 802 can share features with the frame 102, the plurality of fixed blades 806*a*, 806*b*, 806*c*, 806*d* can share features with the plurality of fixed blades 106*a*-106*d*, and the lock actuator 808 can share features with the lock actuator 108.

The surgical retractor device 800 can include four arms 804*a*, 804*b*, 804*c*, and 804*d* that are connected via one or more hinges 810 to form the frame 802. In this embodiment, the arms 804*a*-804*d* can be curved arms that each have equal or nearly equal lengths to each other. The frame 802 is formed as a linkage, such as a four-bar linkage frame that includes the four arms 804*a*, 804*b*, 804*c*, and 804*d*. Similar to the movement previously described in connection with FIGS. 1-2, the frame 802 (FIG. 8) can be used such that movement of two arms relative to one another urges movement of all the arms 804*a*, 804*b*, 804*c*, and 804*d* of the linkage frame. A user can impart movement on any of the arms 804*a*, 804*b*, 804*c*, and 804*d* to urge the movement of the other arms 804*a*, 804*b*, 804*c*, and 804*d*.

Still referring to the embodiment in FIG. 8, the arms 804*a*-804*d* have a plurality of openings 811 that extend through the arms 804*a*-804*d*. The plurality of openings 811 are spaced apart around the perimeter of the frame 802 between each of the fixed blades 806*a*-806*d*. The plurality of openings 811 extend from an outer surface 812 to an inner surface 814 of each of the arms 804*a*-804*d*. Modular accessories can be attached to the frame 802 by extending through at least one of the plurality of openings 811. For example, one or more paddles 840*a*, 840*b* can be attached to the frame 802 by inserting a bar 842*a*, 842*b* of the paddles 840*a*, 840*b* through openings 811 in the frame 802. The paddles 840*a*, 840*b* can be secured to the frame via an interference fit, a fastener, an adhesive, or otherwise attached to the frame 802 to hold the paddles 840*a*, 840*b* in position.

The surgical retractor device 800 can include one or more light sources that illuminate a surgical working area. In some embodiments, the fixed blades 806*a*-806*d* each include at least one light source 820*a*-820*d* and the paddles 840*a*, 840*b* can include at least one light source 860*a*, 860*b*. In the depicted embodiment, the paddles 840*a*, 840*b* each include a plurality of light sources 860*a*, 860*b* that extend along the length of the paddles 840*a*, 840*b*. In some embodiments, the light sources 820*a*-820*d* and 860*a*, 860*b* can include light-emitting diodes (LEDs), optical fibers, fluorescent light sources, or other light sources that facilitate the illumination of the surgical area. The light sources 820*a*-820*d* and 860*a*, 860*b* can be activated to illuminate a surgical working area.

In some embodiments, the surgical retractor 800 includes a power source 864 that powers the light sources 820*a*-820*d* and 860*a*, 860*b*. In some embodiments, the connection of each paddle 840a-840b to the frame 802 provides an electric connection between each of the light sources 860a-860b and the power source 864. In some embodiments, each paddle 840a-840b could include a power source (e.g., power source 864).

Figure 9:
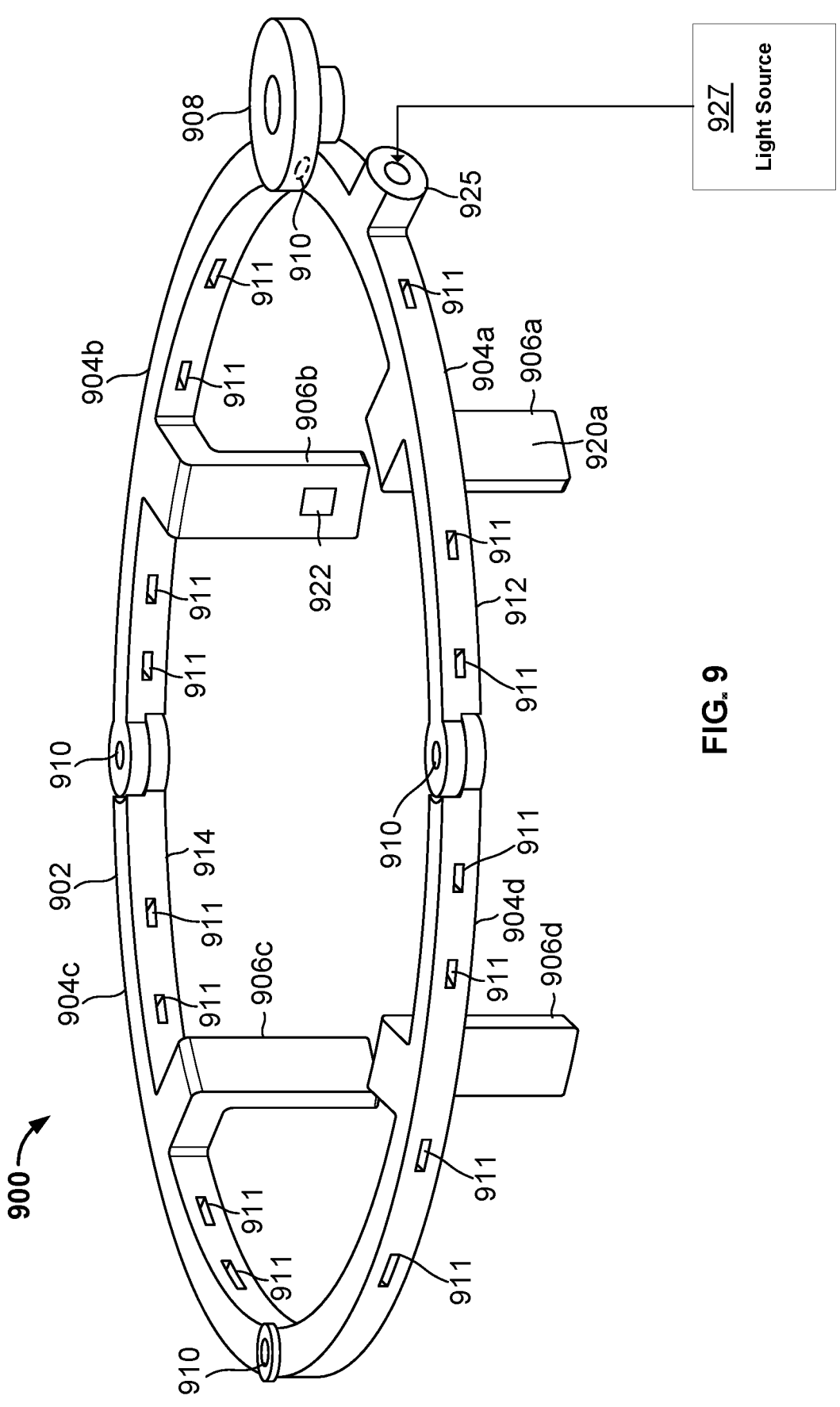
FIG. 9 shows a perspective view of a further example of a surgical retractor device with one or more light sources, consistent with other embodiments of this disclosure.
Figures 10A, 10B, 10C, 10D:
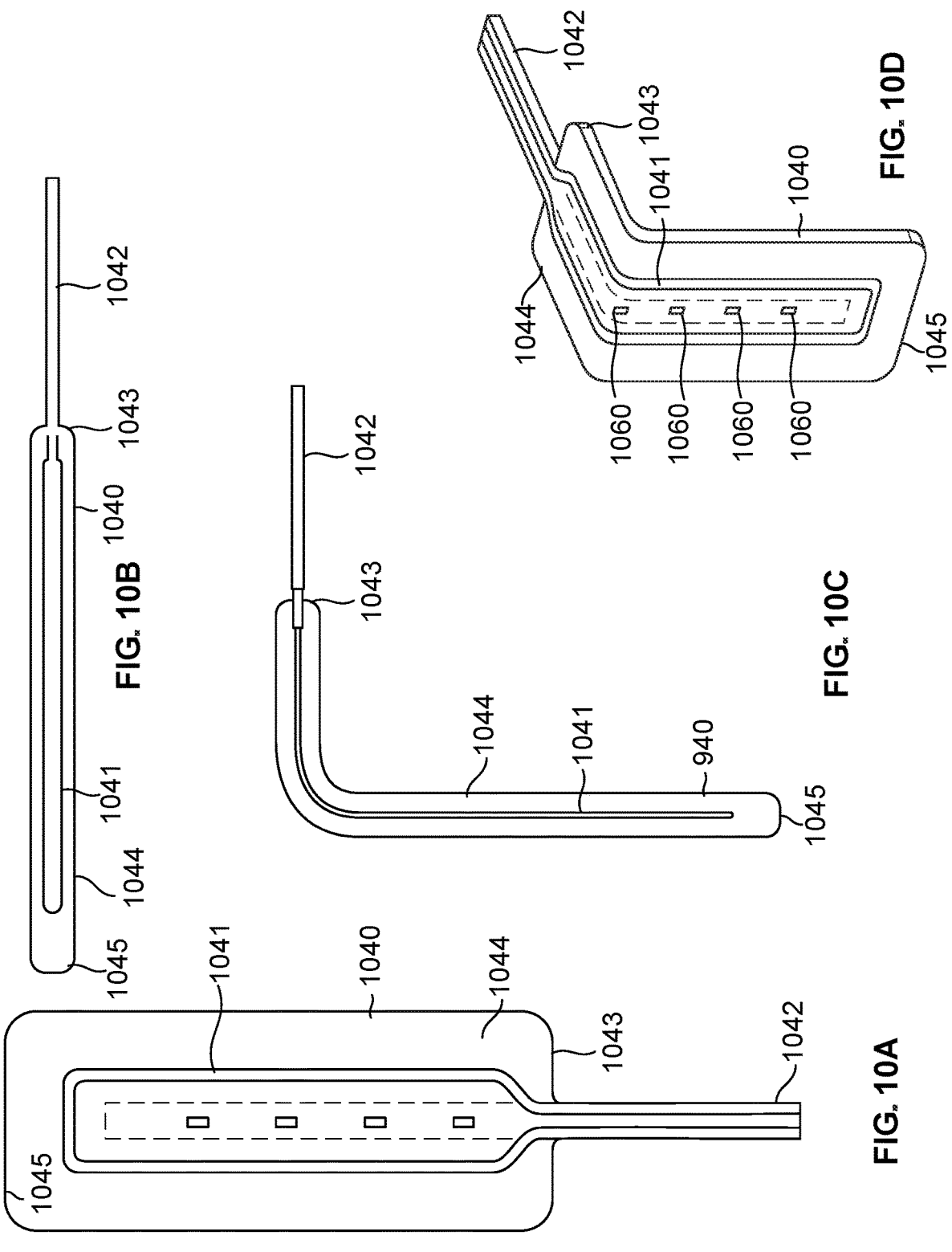
FIGS. 10A-10D show top, side, and perspective view of examples of the modular accessories of FIG. 8 in the form of flexible paddles, consistent with some embodiments of this disclosure.

Referring to FIG. 9, some embodiments of a surgical retractor device 900 are configured to retract various tissue layers of a subject to provide an access opening for medical personnel. The surgical retractor 900 can share features with surgical retractor 800. For example, the surgical retractor 900 includes a frame 902 that shares features with the frame 802, arms 904a-904d that share features with arms 904a-804d, fixed blades 906a-906d that share features with fixed blades 806a-806d, lock actuator 908 that shares features with lock actuator 808, hinges 910 that share features with hinges 810, and openings 911 that share features with openings 811.

In some embodiments, the surgical retractor 900 includes an optical port 925. The optical port 925 can be connected to the frame 902. The optical port 925 can be a light port that is configured to releasably connect to a light source 927. The light source 927 can provide illumination and power to the surgical retractor. For example, the light source 927 can provide power to one or more light emitters of the surgical retractor (e.g., light emitters 820a-820b, 860a, 860b could be implemented in surgical retractor 900), can illuminate the frame 902, can activate optical fibers of the surgical retractor 900, or otherwise provide power and light energy that facilitate the illumination of the surgical area.

The light source 927 can provide power to a camera 922 of the surgical retractor 900 when the light source 927 is connected to the optical port 925. In some embodiments, the camera 922 is connected to at least one of the fixed blades 906a-906d. For example, the camera 922 can be connected to the fixed blade 906b. The camera 922 can include a light emitter that illuminates the field of view of the camera. In some embodiments, the surgical retractor 900 can include more than one camera 922. For example, the surgical retractor device can include two cameras 922, three cameras 922, each fixed blade 906a-906d can include a camera 922, or more cameras 922. The camera 922 (or cameras 922) can provide imaging of the surgical working area that may be obstructed from view, or may be recorded during an operation.

Referring to FIGS. 10A-10D, some embodiments of a flexible paddle (e.g., optionally, such as those described above in connection with FIGS. 8-9) can include a flexible paddle 1040 that is pliable and can be arranged into custom orientations. The flexible paddle 1040 can be a modular accessory that is releasably connectable to and removable from surgical retractor devices (e.g., surgical retractor device 800).

The flexible paddle 1040 can include an internal frame 1041 that is pliable and configured to be bent into a custom orientation and remain in the custom orientation until a user (e.g., a surgeon or other user) bends the flexible paddle 1040 out of the custom orientation into another orientation. The internal frame 1041 can be metallic and flexible to be plastically deformed and maneuvered into custom orientations, while maintaining rigidity to retract tissues and organs when the flexible paddle 1040 is positioned in the custom orientation. In some embodiments, the flexible paddle 1040 can be straight (e.g., FIGS. 10A and 10B), can be bent to around 90 degrees (e.g., FIGS. 10C and 10D), and can be bent into custom configurations at any angle. For example, the flexible paddle 1040 can be bent to form a looped shape where a second end 1045 of the flexible paddle can be bent to contact another portion of the flexible paddle 1040 (e.g., at the first end 1043 or any other location of the paddle 1040). The flexible paddle 1040 can be bent into a hooked shape where the second end 1045 of the flexible paddle can be bent and may not contact another portion of the flexible paddle 1040.

Still referring to FIGS. 10A-10D, the internal frame 1041 of the flexible paddle 1040 can be connected to, extend from, or formed with a bar 1042 that extends from a proximal end 1043 of a paddle surface 1044. In some embodiments, the bar 1042 can connect the flexible paddle 1040 to the surgical retractor 800 or 900 (e.g., FIG. 8 or 9). For example, the bar 1042 can extend through one of the plurality of openings 811 or 911 and releasably connect the flexible paddle 1040 to the surgical retractor 800 or 900.

In some embodiments, the paddle surface 1044 can extend beyond the internal frame 1041 to provide an outer profile of the flexible paddle 1040. For example, the paddle surface 1044 can define a rectangular shape as depicted in FIGS. 10A-10D. The paddle surface 1044 can provide a variety of shapes and sizes of the flexible paddle 1040 including, but not limited to, a rectangular shape, a tapered shape having a greater width at a second end than the first end (see e.g., paddle 840b), a hook shape, among other shapes and sizes. The paddle surface 1044 can be a tissue-contact surface that can be sterilized and used in the surgical working area. For example, the paddle surface 1044 can be a metal surface (e.g., stainless steel), a plastic surface, a rubber surface, and other materials that can be sterilized.

In the depicted embodiment, the flexible paddle 1040 includes a plurality of light sources 1060 that extend along the length of the flexible paddle 1040. In some embodiments, the light sources 1060 can include light-emitting diodes (LEDs), optical fibers, fluorescent light sources, or other light sources that facilitate the illumination of the surgical area. The light sources 1060 can be activated to illuminate a surgical working area.

The flexible paddle 1040 can be a modular accessory that can be implemented in surgical retractor devices (e.g., surgical retractor device 800). The flexible paddle 1040 can improve the user's experience by retracting additional tissues and organs within the surgical working area. For example, the flexible paddle 1040 can contact and retract additional organs, muscles, and other tissue layers that fixed blades do not reach, contact, or retract.

Figure 11A:
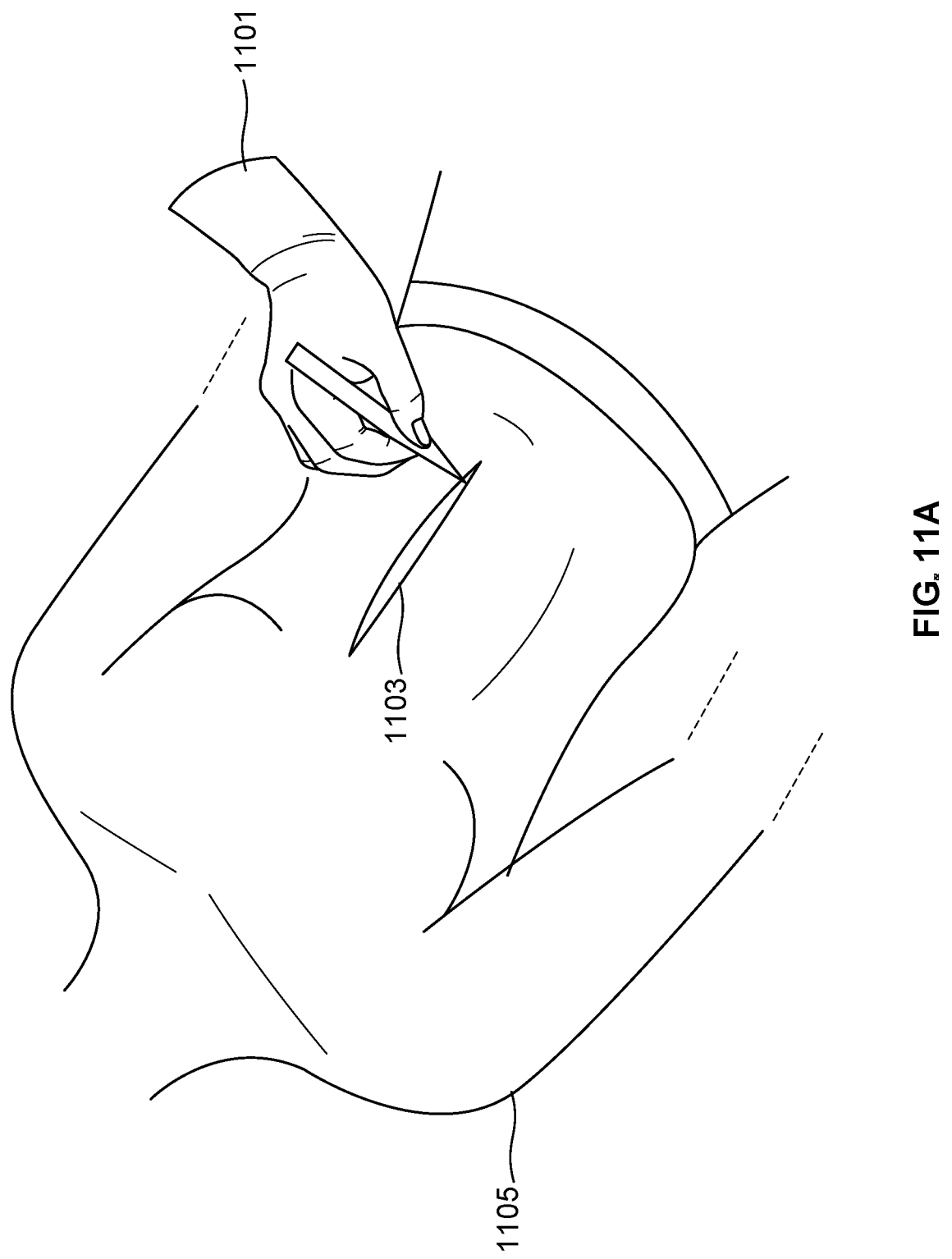
FIGS. 11A-11C show perspective view of an example method of retracting a surgical opening using the surgical retractor device of FIGS. 1-7 (or any of the example retractor devices of FIGS. 8-9 and 12-15), consistent with some embodiments of this disclosure.
Figure 11B:
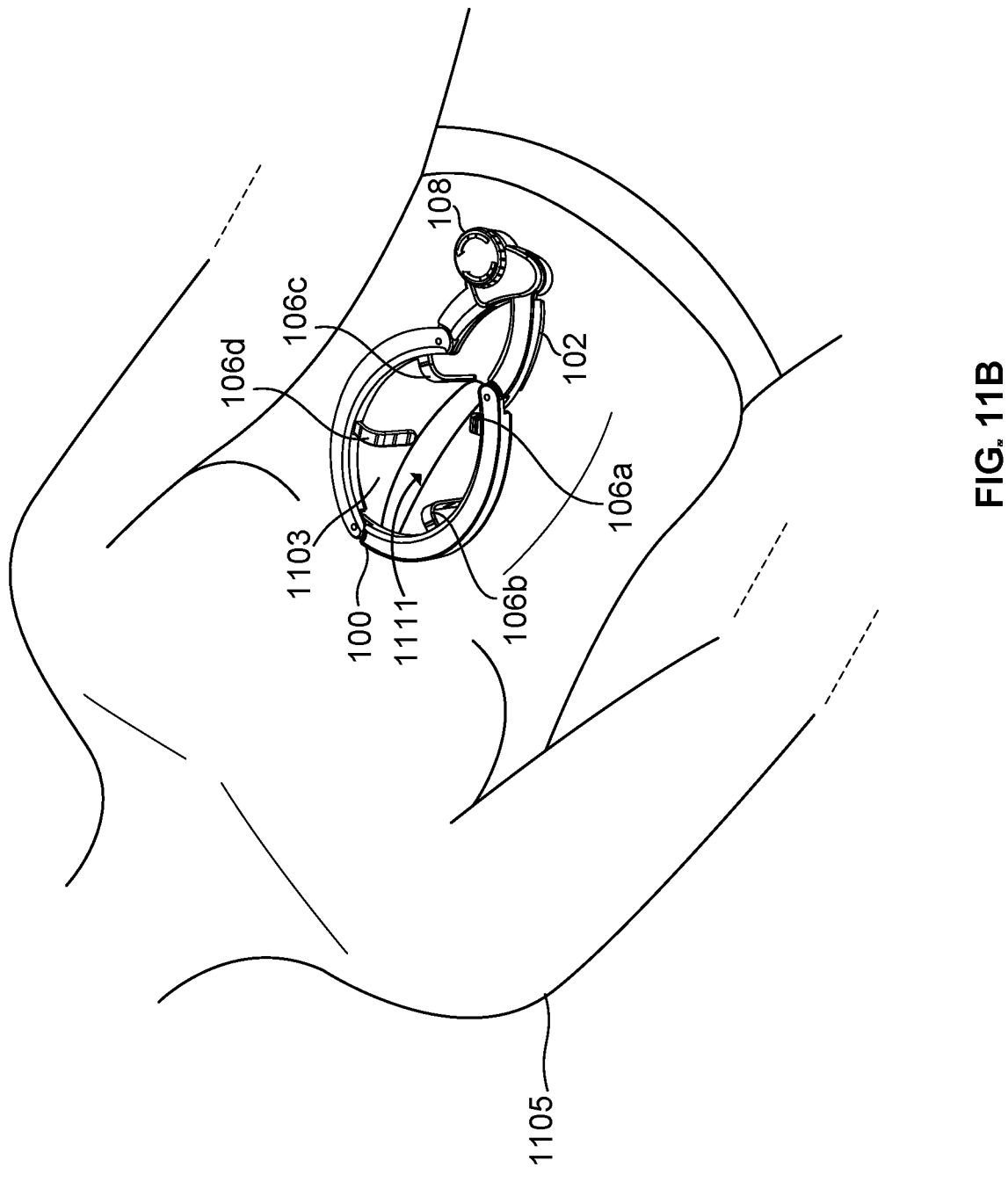
Figure 11C:
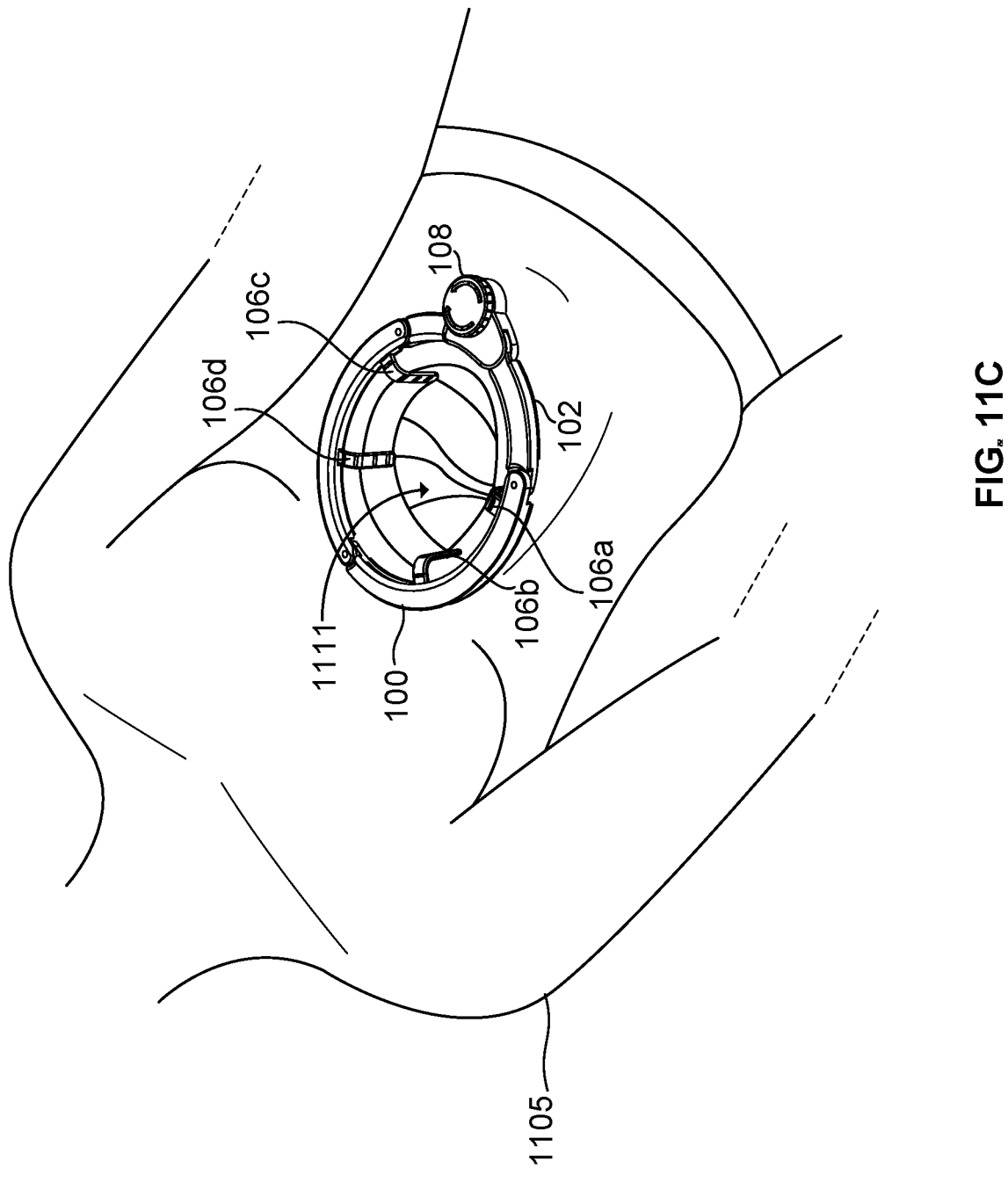

Referring to FIGS. 11A-11C, some embodiments of the surgical retractor device 100 can be rapidly deployed to open and maintain an access opening during a surgical procedure. The surgical retractor 100 is configured for rapid deployment in establishing access opening through which a surgeon can perform an operation upon an internal organ or other bodily tissue. (It should be understood from the description herein that the method depicted in FIGS. 11A-C is described for illustrative purposes with the retractor device 100 of FIGS. 1-7, but the retractor device 800 or 900 (FIGS. 8-10D) or the retractor device 1200 (FIGS. 12-15) can likewise be used in the depicted method to rapidly deploy and maintain an access opening during a surgical procedure.)

Referring to FIG. 11A, some embodiments of a surgical procedure include a surgeon 1101 creates an incision 1103 in an abdomen of a patient 1105. While an incision 1103 is shown in the abdomen of the patient, the incision 1103 could occur elsewhere on the patient 1105 such as in the chest, in the back, in one or more limbs, among other locations. The surgical retractor 100 can be utilized without an incision 1105. For example, the surgical retractor 100 can be utilized to retract other orifices such as a mouth of a patient.

Referring to FIG. 11B, some embodiments of the surgical retractor 100 in the collapsed position can be inserted into the incision 1103. The surgical retractor 100 can partially open the incision 1103 in the collapsed position, where the fixed blades 106a-106d engage with initial tissue layers (e.g., skin, fascia, muscle) adjacent to the incision 1103 to pull the incision 1103 apart and partially open an access opening 1111.

Referring to FIG. 11C, some embodiments of the surgical retractor 100 can be expanded into the expanded position to fully open the access opening 1111. The fixed blades 106a-106d remain engaged with the tissue layers (e.g., skin, fascia, muscle) of the incision 1103 during expansion of the frame 102 from the collapsed position to the expanded position. The frame 102 and the arms can remain exterior to the access opening 1111 and the incision 1103 while the fixed blades 106a-106d extend into the access opening 1111. The lock actuator 108 can be actuated from the unlocked position to the locked position to maintain the access opening 1111. The lock actuator 108 can be unlocked to adjust the shape and size of the access opening 1111 by actuating one or more arms of the frame 102. The frame 102 is formed as a linkage, and a user can impart movement on any of the arms of the frame 102 to urge the movement of the other arms. Additionally, the lock actuator 108 can be unlocked to remove the surgical retractor 100.

In some embodiments, after expansion of the surgical retractor 100 to an expanded position, one or more modular accessories can be releasably connected to the surgical retractor device 100. For example, flexible paddles such as flexible paddles 140a-140f and surgical drape 150 (refer to FIGS. 4-7) can be attached to the surgical retractor 100 when the surgical retractor is maintaining the access opening 1111. Each of the modular accessories can be independently adjusted to provide customized retraction and lighting of the surgical operating area in the access opening 1111. The modular accessories can also be implemented in some example embodiments, and the modular accessories can retract tissues and organs within the surgical working area in addition to the tissues retracted by the fixed blades 106a-106d. The modular accessories can illuminate the surgical area without the intervention of a separately inserted lighting instrument that might otherwise obstruct or occupy portions of the access opening.

Still referring to FIG. 11C, some embodiments of the surgical retractor 100 can be structured as a patient-anchored retractor device (e.g., without requiring a mechanical anchor to the operating table extending from the operating table). For example, the surgical retractor 100 can independently maintain the access opening 1111 in the locked positon without any articulating arm or other mechanical anchor that secures the retractor 100 to the operating table. In the depicted embodiment and as described above, the frame 102 may be constructed free of mounting holes or other external mounts to matingly receive to a table anchor structure, such as a lockable articulating arm extending from the operating table. Thus, as shown in the example in FIGS. 11A-C, the surgical retractor 100 can be implemented in a rapidly deployable manner that maintains the access opening 1111 throughout the duration of a surgery without requiring mechanical external anchoring to an operating table, which can reduce the amount of tasks in mounting the retractor device and can reduce the amount of mechanical obstructions in surgical area extending from the retractor device.

Figure 12:
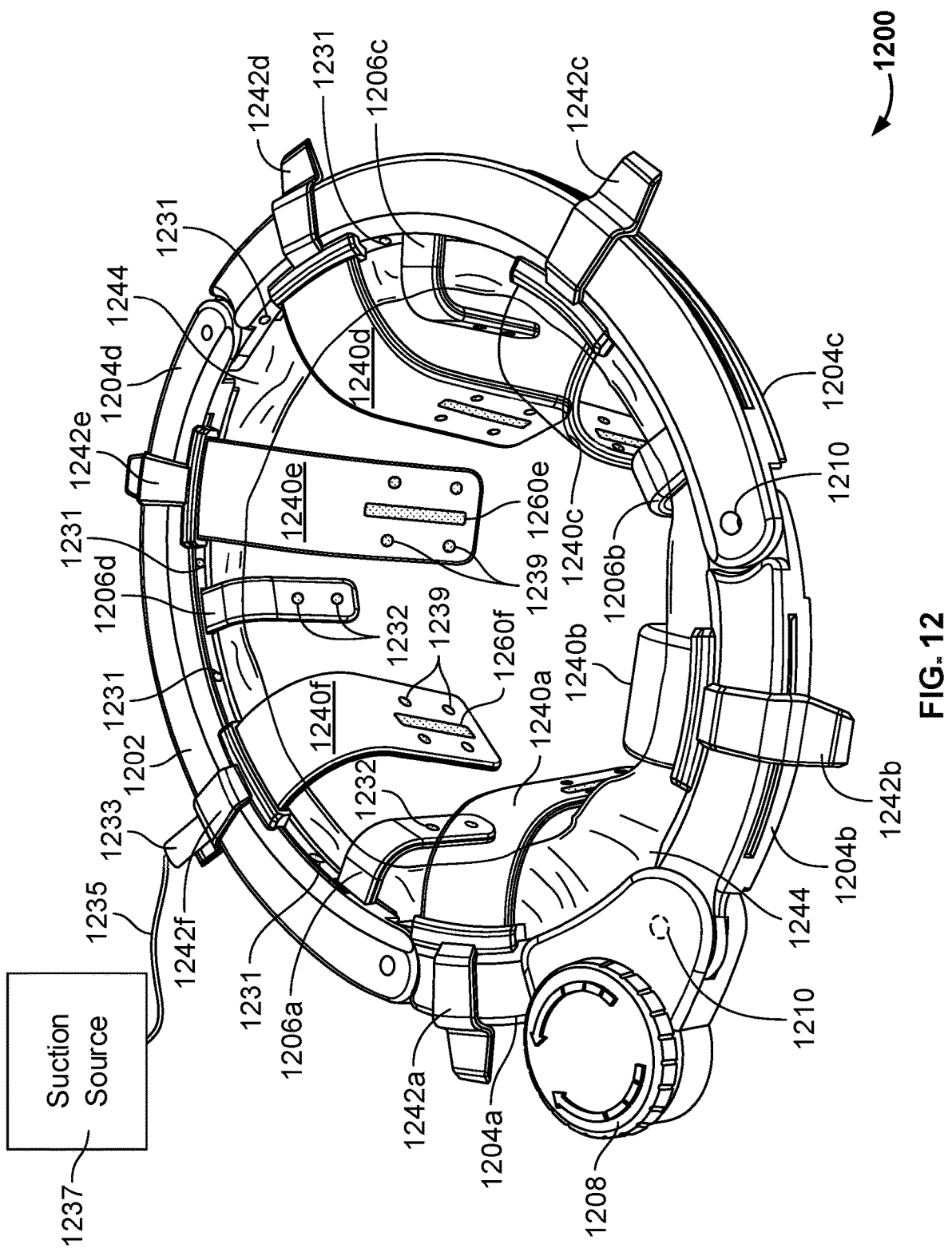
FIG. 12 shows a perspective view of an example surgical retractor device that is configured to withdraw vapor from a surgical area, consistent with some embodiments of this disclosure.

Referring to FIG. 12, some examples of a surgical retractor device 1200 are configured to retract various tissue layers of a subject to provide an access opening for medical personnel and, optionally, to beneficially remove vapor (or other fluids that might obscure the surgeon's field of view) from the access opening. As shown in FIG. 12, the surgical retractor 1200 can share features with surgical retractor 100 previously described in FIG. 1-7. For example, the surgical retractor 1200 includes a frame 1202 that shares at least some features with the frame 102, arms 1204a-1204d that share features with arms 104a-104d, fixed blades 1206a-1206d that share features with fixed blades 106a-106d, lock actuator 1208 that shares features with lock actuator 108, hinges 1210 that share features with hinges 110, and flexible paddles 1240a-1240f that share features with flexible paddles 104a-140f.

In some embodiments, vapor 1244 can be obstructive to the field of view of a surgeon or other personnel of the access opening maintained by the surgical retractor device 1200. For example, the vapor 1244 can be bodily gasses, smoke from tissue cauterization procedures, or other vapors that obstruct the field of view into the access opening as defined by the surgical retractor device 1200. In the depicted embodiment, the surgical retractor device 1200 includes one or more suction ports in at least one of the frame 1202, the fixed blades 1206a-1206d, and the flexible paddles 1240a-1240d to remove the vapor 1244 from the access opening. The suction ports in at least one of the frame 1202, the fixed blades 1206a-1206d, and the flexible paddles 1240a-1240d facilitate aspiration of the vapor 1244 from the access opening. Optionally, some or all of the suction ports in at least one of the fixed blades 1206a-1206d and the flexible paddles 1240a-1240d can be located within the access opening at a located that is further configured to aspirate other fluids (e.g., bodily gasses, smoke, saline, or blood) that might also obscure the surgeon's field of view.

Optionally, the frame 1202 includes a plurality of openings 1231 positioned along an inner profile 1214 of the frame 1202 to provide a set of suction ports. The plurality of openings 1231 can be spaced apart around the inner profile 1214 of the frame 1202 such that each of the arms 1204a-1204d includes at least one of the plurality of openings 1231. Each of the openings 1231 are connected to a suction outlet 1233 that connects to a suction source 1237 via a conduit 1235. The suction source 1237 applies suction and/or pneumatic vacuuming to the plurality of openings 1231 (e.g., via tubing, conduit, channels, through the frame 1202). The suction at each of the plurality of openings 1231 can facilitate the removal of vapor 1234 positioned in the access opening maintained by the surgical retractor device 1200.

In some embodiments, the fixed blades 1206a-1206d can include a plurality of openings 1232 to provide another set of suction ports. The plurality of openings 1232 can be positioned along an internal side of the fixed blades 1206a-1206d that faces towards the working area of the access opening. The plurality of openings 1232 can be spaced apart along the fixed blades 1206a-1206d and can provide suction at varying depths within the access opening. In some embodiments, the fixed blades 1206a-1206d can include one opening 1232, two openings 1232, or three or more openings 1232.

In some embodiments, one of the fixed blades 1206a-1206d (e.g., fixed blade 1206d) can include openings 1232 and the other fixed blades (e.g., fixed blades 1206a-1206c) do not include the openings 1232. In some embodiments, two of the fixed blades 1206a-1206d include the openings 1232. In some embodiments, three of the fixed blades 1206*a*-1206*d* include the openings 1232. In some embodiments, each of the fixed blades 1206*a*-1206*d* include the openings 1232. Each of the openings 1232 are connected to the suction outlet 1233 that connects to the suction source 1237 via the conduit 1235. The suction source 1237 applies suction and/or pneumatic vacuuming to the plurality of openings 1232 (e.g., via tubing, conduit, channels, through the frame 1202 and the fixed blades 1206*a*-1206*d*). The suction at each of the plurality of openings 1232 can facilitate the removal of vapor 1234 positioned in the access opening maintained by the surgical retractor device 1200.

Optionally, the flexible paddles 1240*a*-1240*f* can include a plurality of openings 1239 to provide a set of suction ports. The plurality of openings 1239 can be positioned along an internal side of the flexible paddles 1240*a*-1240*f* that faces towards the working area of the access opening. The plurality of openings 1239 can be spaced apart along the flexible paddles 1240*a*-1240*f* and can provide suction at varying depths within the access opening. In some embodiments, the flexible paddles 1240*a*-1240*f* can include one opening 1239, two openings 1239, or three or more openings 1239. The openings 1239 can be arranged as pairs of openings 1239 that are positioned on opposing sides of a light source of the flexible paddles 1240*a*-1240*f* (e.g., light source 1260*f*).

In some embodiments, one of the flexible paddles 1240*a*-1240*f* (e.g., flexible paddle 1240*f*) can include openings 1239 and the other flexible paddles (e.g., flexible paddles 1240*a*-1240*e*) do not include the openings 1239. In some embodiments, two of the flexible paddles 1240*a*-1240*f* (e.g., flexible paddles 1240*e*, 1240*f*) include the openings 1239. In some embodiments, three of the flexible paddles 1240*a*-1240*f* include the openings 1239. In some embodiments, each of the flexible paddles 1240*a*-1240*f* include the openings 1239. Each of the openings 1239 are connected to the suction outlet 1233 that connects to the suction source 1237 via a conduit 1235. The suction source 1237 applies suction and/or pneumatic vacuuming to the plurality of openings 1239 (e.g., via tubing, conduit, channels, through the frame 1202 and the flexible paddles 1240*a*-1240*f*). The suction at each of the plurality of openings 1232 can facilitate the removal of vapor 1234 positioned in the access opening maintained by the surgical retractor device 1200.

In some embodiments, any of the frame 1202, the fixed blades 1206*a*-1206*d*, and the flexible paddles 1240*a*-1240*f* can include openings that connect to the suction source 1237 (e.g., openings 1231, 1232, 1239). For example, the flexible paddles 1240*a*-1240*f* can include openings 1239 while the frame 1202 and the fixed blades 1206*a*-1206*d* do not include openings. The flexible paddles 1240*a*-1240*f* having openings 1239 facilitate a modular vapor aspiration accessory that can be added and removed from the surgical retractor device 1200 as desired by the surgeon or other operator.

Figure 13:
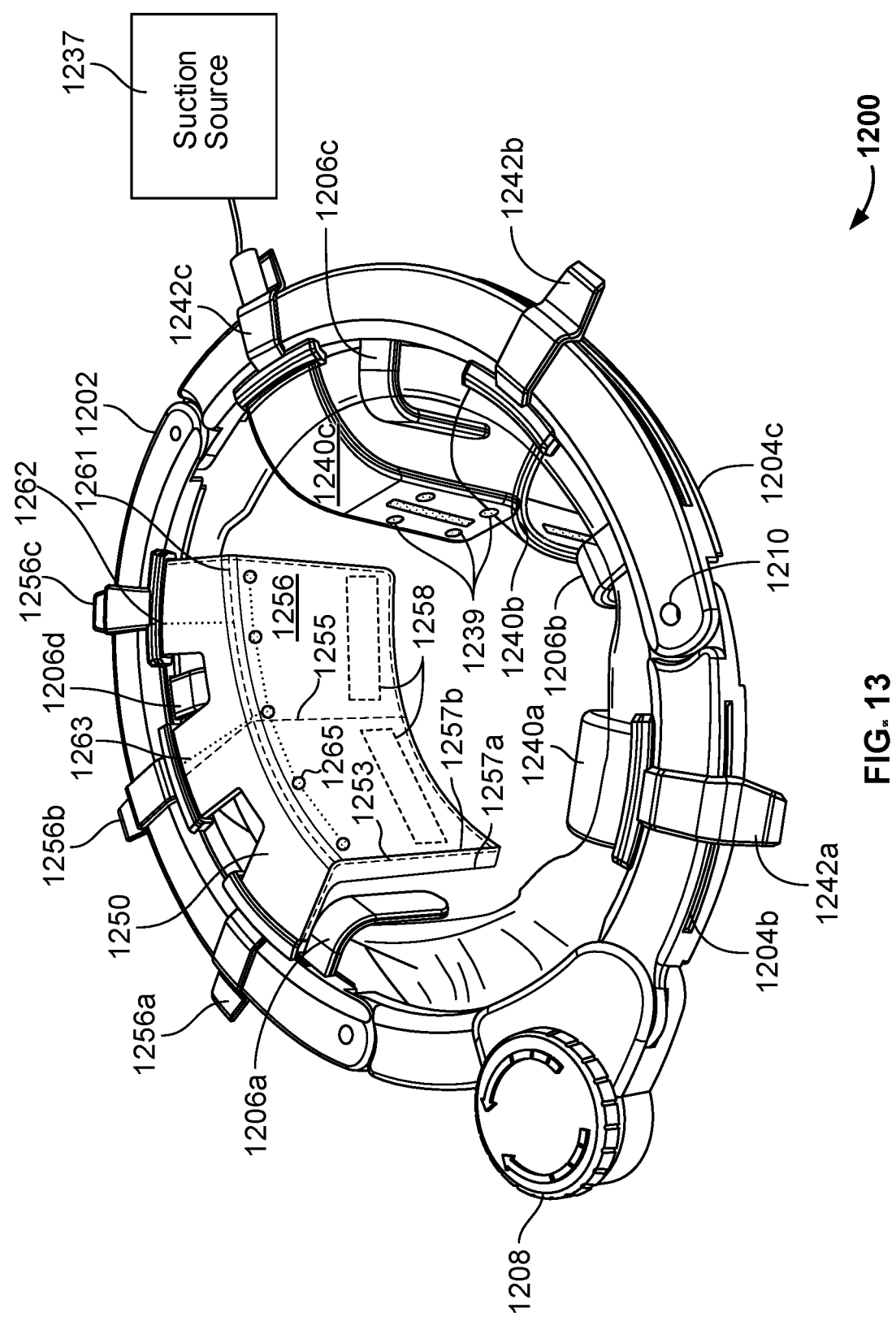
FIG. 13 shows a perspective view of an example retractor device with flexible paddles and a retractor drape, consistent with some embodiments of this disclosure.

FIG. 13 shows the retractor device 1200 with one or more additional modular accessories such as flexible paddles 1240*a*-1240*c* and a surgical drape 1250. In some embodiments, the surgical drape 1250 is connected to the frame 1202. The surgical drape 1250 can attach to the frame 1202 via one or more brackets 1252*a*-1252*c*. The brackets 1252*a*-1252*c* can share the features of the brackets 1242*a*-1242*c* that attach the plurality of flexible paddles 1240*a*-1240*c* to the frame 1202.

In some aspects, the surgical drape 1250 includes three brackets 1252*a*-1252*c* that facilitate connection and removal of the surgical drape 1250 to and from the frame 1202. While three brackets 1252*a*-1252*c* are depicted, other embodiments could include one bracket (e.g., bracket 1252*b*), two brackets (e.g., brackets 1252*a* and 1252*c*), or more than three brackets.

In some embodiments, the surgical drape 1250 can extend over one or more of the fixed blades (e.g., fixed blade 1206*d*) to provide at least one of a covering, padding, shielding, or otherwise partitioning a portion of the surgical retractor device 1200. For example, the surgical drape 1250 can cover a portion of an access opening that medical personnel to prevent exposure of that portion of the access opening to treatment or operations performed in other areas of the access opening. The surgical drape 1250 can provide additional retraction of tissue layers to supplement the tissue retraction of the fixed blades 1206*a*-1206*d* and the flexible paddles 1240*a*-1240*c*. For example, the surgical drape 1250 can provide a continuous surface that prevents tissues from extending between the fixed blades 1206*a*-1206*d* and the flexible paddles 1240*a*-1240*c*.

In some embodiments, the surgical drape 1250 includes a drape frame 1253 that extends around the perimeter of the surgical drape 1250. The drape frame 1253 can include a partition support 1255 that can extend through a middle or near a middle of the drape frame 1253. The drape frame 1253 can include a plurality of support members such as wires, bars, cables, or other support members. The plurality of support members of the drape frame 1253 can be pliable support members that are formable into various shapes and positions to facilitate adjustable and customizable covering, padding, shielding, or otherwise partitioning a portion of the access opening maintained by the surgical retractor device 1200.

In some embodiments, the surgical drape 1250 includes a drape bag 1256 that surrounds the drape frame 1253. The drape bag 1256 includes a sealable membrane that has at least two layers (e.g., outer layer 1257*a* and inner layer 1257*b*) that the drape frame 1253 is positioned between. The drape bag 1256 can receive one or more fillers 1258 that are positioned between the outer layer 1257*a* and the inner layer 1257*b*. In some embodiments, the fillers 1258 can include sponges, surgical sponges, laparotomy pads, gauze, padding, or other filler materials. The fillers 1258 can be held in position within the drape bag 1256 by the drape frame 1253. For example, the partition support 1255 can maintain the positioning of fillers on each side of the partition support 1255. The surgical drape 1250 can have one filler 1258, two fillers 1258, or three or more fillers 1258.

In some embodiments, the drape bag 1256 can be sealed along a top end 1261 of the drape bag 1256. For example, the drape bag 1256 can be open to receive one or more fillers 1258 in the drape bag 1256, and can be closed and sealed to retain the fillers 1258 within the drape bag 1256. The drape bag 1256 can be sealed by a zipper, an interlocking groove and ridge, adhesive, heat seal, or otherwise sealed to close the drape bag 1256.

In some embodiments, the drape bag 1256 can be connected to the suction source 1237 to facilitate suction of the drape bag 1256. Suction of the drape bag 1256 can facilitate an increased rigidity of the drape bag 1256 and the fillers 1258 when the drape bag 1256 is sealed with suction applied by the suction source 1237. For example, the suction of the drape bag 1256 can squeeze the drape bag 1256 and the fillers 1258 from an expanded positon to a compressed position that increases the rigidity of the surgical drape 1250 in relation to the rigidity of the surgical drape in the expanded position.

In some embodiments, the surgical drape 1250 connects to the suction source 1237 to additionally facilitate vapor aspiration through the surgical drape 1250. For example, the surgical drape 1250 can include a seal connection 1262 and an aspiration connection 1263 to the suction source 1237. The seal connection 1262 facilitates the suction of the drape bag 1256 that creates increased rigidity of the surgical drape 1250. The aspiration connection 1263 facilitates vapor removal from the access opening.

In some embodiments, the surgical drape 1250 can include one or more openings 1265 that facilitate vapor aspiration through the surgical drape 1250. The one or more openings 1265 connect to the suction source 1237 via the aspiration connection 1263 that can be fluidly separated and sealed from the drape bag 1256. Each of the openings 1265 are connected to the suction outlet 1233 that connects to the suction source 1237 via conduit 1235. The suction source 1237 applies suction and/or pneumatic vacuuming to the plurality of openings 1265 (e.g., via tubing, conduit, channels, through the frame 1202 and the aspiration connection 1263). The suction at each of the plurality of openings 1265 can facilitate the removal of vapor 1234 positioned in the access opening maintained by the surgical retractor device 1200.

Figure 14:
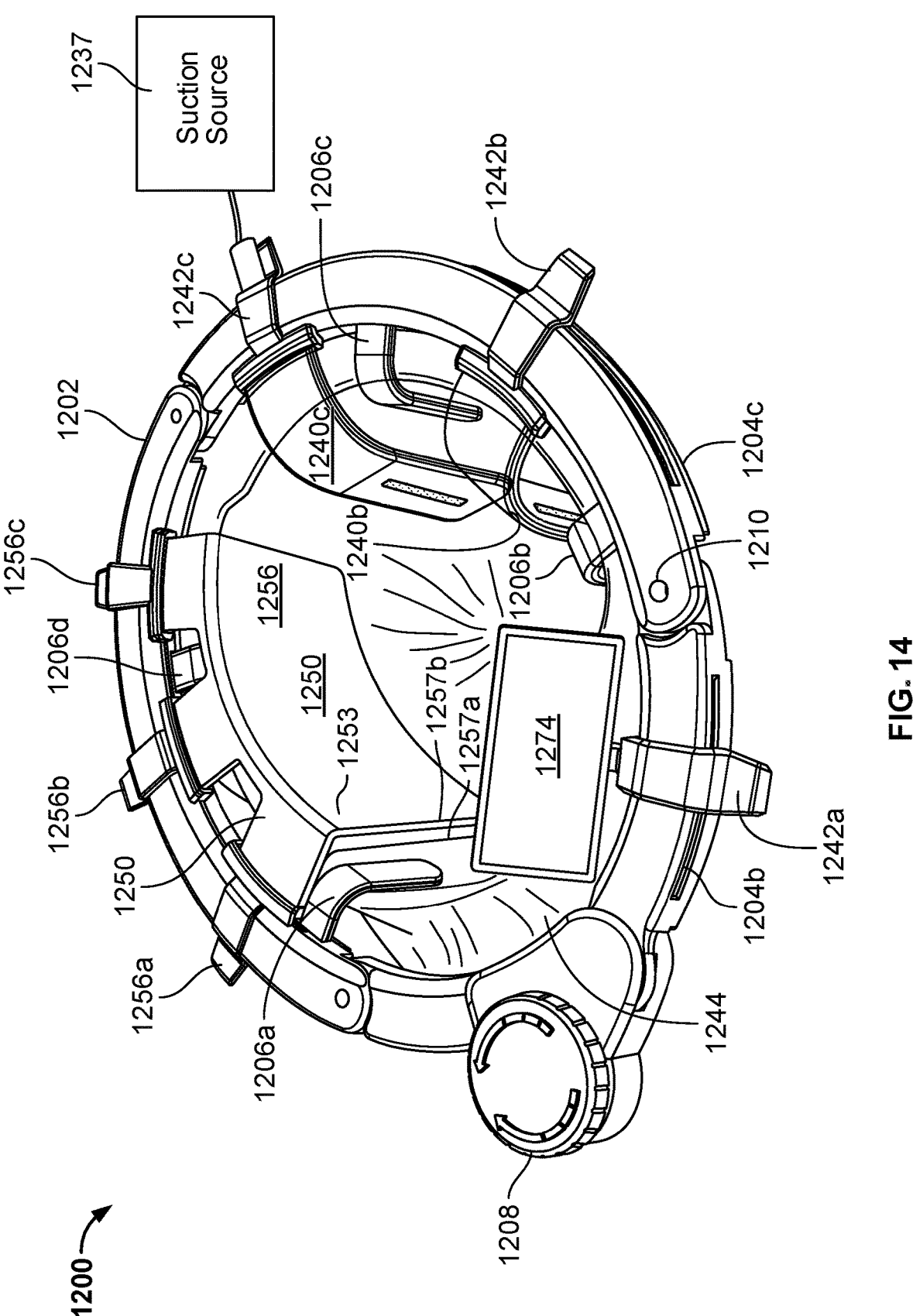
FIG. 14 shows a perspective view of an example retractor device with an imaging device, consistent with some embodiments of this disclosure.
Figure 15:
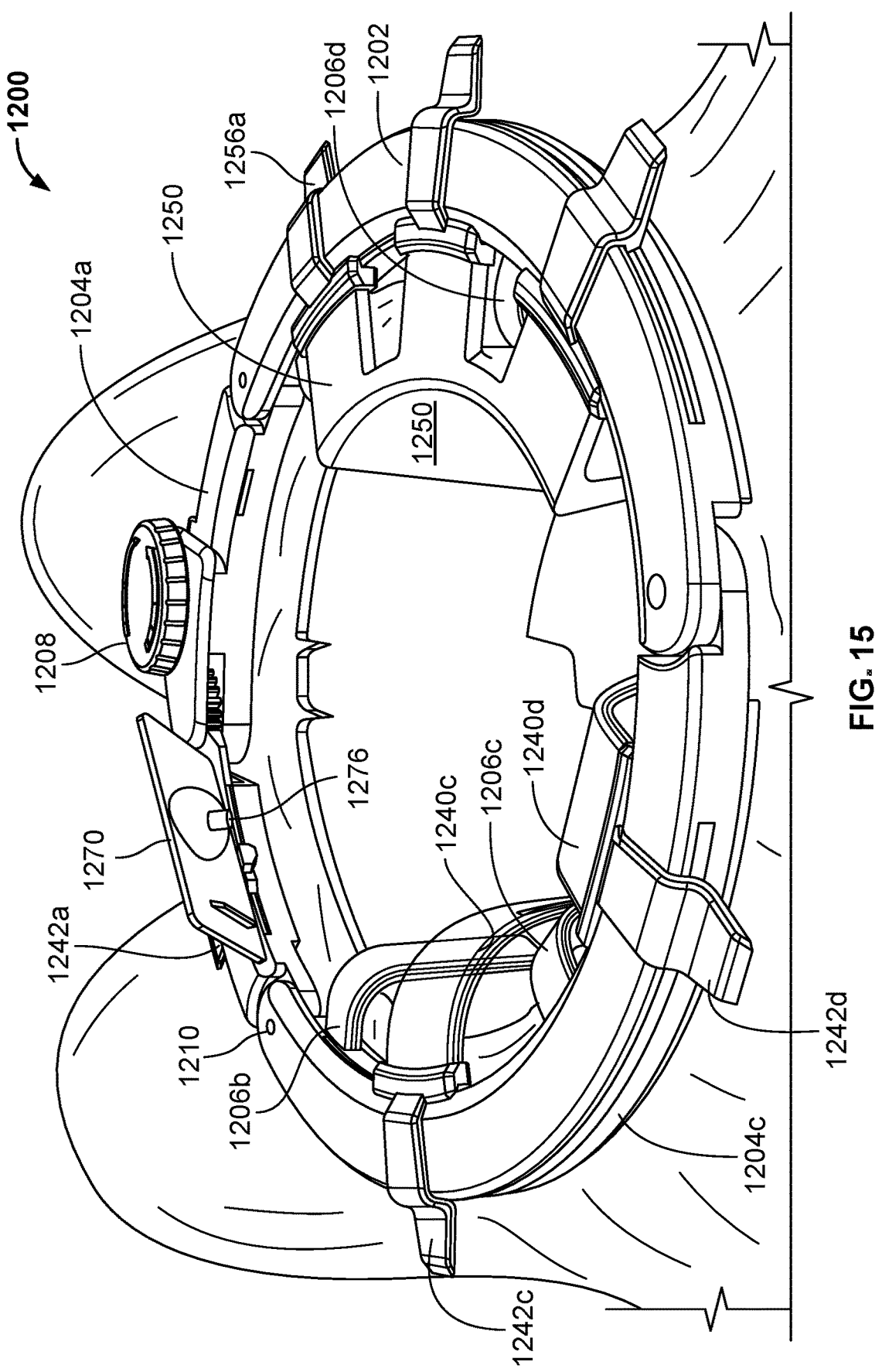
FIG. 15 shows a perspective view of the example surgical retractor device of FIG. 14, consistent with some implementations of an example method of retracting a surgical opening.

Referring to FIGS. 14 and 15, some embodiments of the retractor device 1200 can include multiple types of modular accessories for releasably connection with the frame 1202, including at least one of flexible paddles 1240a-1240c, the surgical drape 1250, and an imaging device 1270. In some embodiments, the imaging device 1270 is connected to the frame 1202. The surgical drape 1250 can attach to the frame 1202 via a brackets 1272a. The bracket 1272a can share the features of the brackets 1242a-1242c that attach the plurality of flexible paddles 1240a-1240c to the frame 1202.

In some embodiments, the imaging device 1270 includes a display 1274 that is oriented away from the access opening (e.g., toward a user). The display 1274 can be articulated with respect to the bracket 1272a to adjust the orientation of the display 1274. For example, the display 1274 can be connected via a ball-and-socket connection to the bracket 1272a that facilitates articulation of the display 1274 to adjust the orientation of the display 1274. The display 1274 can display video, images (including magnified images), or combinations thereof from one or more imaging sources (e.g., imaging source 1276).

In some embodiments, the imaging device 1270 includes an imaging source 1276 mounted opposite from the display 1274 so that is oriented toward the access opening when the display is oriented away from the access opening. The imaging source 1276 can be connected to the bracket 1272a directly or via connection to the display 1274 that is connected to the bracket. For example, the imaging source 1276 can be connected via a ball-and-socket connection to the bracket 1272a that facilitates articulation of the imaging source 1276 to adjust the field of view of the imaging source 1276. The imaging source 1276 can capture images and video of a surgical working area of the access opening maintained by the surgical retractor device 1200.

In some embodiments, the imaging source 1276 can be a camera that can capture images and video in various wavelengths of light. For example, the imaging source 1276 can capture images and video in visible light, ultraviolet light, and infrared light. The imaging source 1276 can be connected to or wirelessly transmit imaging data (e.g., including images and video captured by the imaging source 1276) to one or more displays. For example, the imaging source 1276 can send imaging data to the display 1274 that can show the video and/or images in real-time during a procedure. In some embodiments, the imaging source 1276 transmits or otherwise communicates (e.g., via wireless or wired communication) images and/or video to one or more external displays that are not directly attached to the frame 1202. In some embodiments, the external displays can include operating room displays that a medical provider can reference during a procedure.

In some embodiments, the imaging source 1276 can operate in different modes to capture images and video in visible light, non-visible light, ultraviolet light, and infrared light. For example, the imaging source 1276 can be operable in a first mode where the imaging source 1276 captures visible light and the imaging source 1276 can be switched into a second mode where the imaging source 1276 captures ultraviolet light. In some embodiments, one or more tumor markers can be illuminated in the second mode and the surgeon can precisely operate within the access opening with the imaging source 1276 capturing and displaying the one or more tumor markers during operation. In some embodiments, the imaging device 1270 facilitates hands-free imaging of the access opening.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Although a few implementations have been described in detail above, other modifications are possible. Moreover, other mechanisms for performing the systems and methods described in this document may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A surgical retractor device comprising:
   a four-bar linkage frame that includes four curved arms that are adjustable with respect to each other;
   at least four fixed blades that extend from the four curved arms and in a direction below the four-bar linkage frame; and
   a lock actuator movably attached to one of the four curved arms at an upwardly facing position above the four-bar linkage frame to adjust a clamp that retains the four-bar linkage frame in a user-selected position, the lock actuator is moveable relative to said one of the four curved arms between a locked position and an unlocked position, wherein the four-bar linkage frame further includes four hinge connection joints located between adjacent arms of the four curved arms such that movement of any of the four curved arms urges movement of the other curved arms, wherein the four fixed blades are rigidly and fixedly mounted to two of the four curved arms at positions spaced apart from the four hinge connection joints of the four-bar linkage frame.

2. The surgical retractor device of claim 1, further comprising one or more flexible paddles that are removably attachable to the four-bar linkage frame.

3. The surgical retractor device of claim 2, wherein the one or more flexible paddles are longer than the fixed blades.

4. The surgical retractor device of claim 2, wherein the one or more flexible paddles include a light source.

5. The surgical retractor device of claim 1, wherein the four curved arms comprises a first set of arms and a second set of arms, the second set of arms being longer than the first set of arms.

6. The surgical retractor device of claim 1, wherein the fixed blades comprise at least one light source.

7. A surgical retractor device comprising:

a four-bar linkage frame that includes four curved arms that are adjustable with respect to each other;

at least four fixed blades that extend from the four curved arms and in a direction below the four-bar linkage frame; and a lock actuator movably attached to one of the four curved arms at an upwardly facing position above the four-bar linkage frame to adjust a clamp that retains the four-bar linkage frame in a user-selected position, the lock actuator is moveable relative to said one of the four curved arms between a locked position and an unlocked position, wherein the four curved arms comprises a first set of arms and a second set of arms, the second set of arms being longer than the first set of arms, and wherein the fixed blades extend from the second set of arms.

8. A surgical retractor device comprising:

a frame that includes a plurality of arms that are adjustable with respect to each other;

a plurality of fixed blades that extend from an inner profile of the plurality of arms at permanently fixed positions spaced apart from connections between the plurality of arms;

one or more flexible paddles releasably mounted to the frame between the fixed blades;

a light port that receives a light source connection, wherein light emitting elements within one or more of the fixed blades and the flexible paddles illuminate in response to light energy delivery from the light port; and a lock actuator that controls adjustability of the arms, the lock actuator is moveable between a locked position and an unlocked position, wherein:

responsive to the lock actuator being moved into the unlocked position, the frame is adjustable between a collapsed position and an expanded position; and responsive to the lock actuator being moved into the locked position, the frame is locked in a position the plurality of arms are in when the lock actuator is moved into the locked position.

9. The surgical retractor device of claim 8, wherein the surgical retractor device is adjustable between a collapsed position and an expanded position by adjusting the plurality of arms with respect to each other, and the frame is lockable at a plurality of positions from the collapsed position to the expanded position.

10. The surgical retractor device of claim 8, wherein movement of any of the plurality of arms urges movement of the other arms.

11. The surgical retractor device of claim 8, wherein the one or more flexible paddles are longer than the fixed blades.

12. A surgical retractor device comprising:

a frame that includes a plurality of arms interconnected by hinge connection joints such that the plurality of arms are adjustable with respect to each other;

a plurality of fixed blades non-releasably mounted to the plurality of arms at fixed locations spaced apart from said connection joints between the plurality of arms, the plurality of blades having a first length; and one or more flexible paddles releasably mounted to the frame between the fixed blades, the flexible paddles having a second length that is longer than the first length;

wherein the first length is configured for retracting at least one of skin, muscle, and fascia, and the second length is configured for retracting tissues at a greater depth than the first length.

13. The surgical retractor device of claim 12, wherein the surgical retractor device is adjustable between a collapsed position and an expanded position by adjusting the plurality of arms with respect to each other, and the frame is lockable at a plurality of positions from the collapsed position to the expanded position.

14. The surgical retractor device of claim 12, further comprising a lock actuator that controls adjustability of the arms, the lock actuator is moveable between a locked position and an unlocked position.

15. The surgical retractor device of claim 14, wherein:

responsive to the lock actuator being moved into the unlocked position, the frame is adjustable between a collapsed position and an expanded position; and responsive to the lock actuator being moved into the locked position, the frame is locked in a position the plurality of arms are in when the lock actuator is moved into the locked position.

16. The surgical retractor device of claim 12, wherein movement of any of the plurality of arms urges movement of the other arms.

* * * * *